United States Patent
Tanaka et al.

(10) Patent No.: US 11,253,157 B2
(45) Date of Patent: Feb. 22, 2022

(54) BIOLOGICAL DATA MEASUREMENT DEVICE

(71) Applicant: TECHNO-COMMONS, INC., Nagano (JP)

(72) Inventors: Akio Tanaka, Hyogo (JP); Chun Kit Chan, Hyogo (JP); Kohei Higuchi, Hyogo (JP)

(73) Assignee: TECHNO-COMMONS INC., Nagano (JP)

( * ) Notice: Subject to any disclaimer, the term of this patent is extended or adjusted under 35 U.S.C. 154(b) by 336 days.

(21) Appl. No.: 16/201,462

(22) Filed: Nov. 27, 2018

(65) Prior Publication Data

US 2019/0159680 A1 May 30, 2019

(30) Foreign Application Priority Data

Nov. 30, 2017 (JP) .............................. JP2017-231112

(51) Int. Cl.

| | |
|---|---|
| *G01J 5/00* | (2006.01) |
| *G01K 15/00* | (2006.01) |
| *G01K 1/00* | (2006.01) |
| *G01K 13/00* | (2021.01) |
| *A61B 5/01* | (2006.01) |
| *A61B 5/0533* | (2021.01) |
| *A61B 5/0205* | (2006.01) |
| *A61B 5/00* | (2006.01) |
| *A61B 5/024* | (2006.01) |
| *A61B 5/259* | (2021.01) |
| *A61B 5/282* | (2021.01) |

(52) U.S. Cl.
CPC ............... *A61B 5/01* (2013.01); *A61B 5/024* (2013.01); *A61B 5/02055* (2013.01); *A61B 5/0533* (2013.01); *A61B 5/259* (2021.01); *A61B 5/282* (2021.01); *A61B 5/6831* (2013.01); *A61B 2562/0271* (2013.01); *A61B 2562/16* (2013.01)

(58) Field of Classification Search
USPC .............................. 374/121, 1, 141, 208, 142
See application file for complete search history.

(56) References Cited

U.S. PATENT DOCUMENTS

| | | | | |
|---|---|---|---|---|
| 2003/0111605 A1* | 6/2003 | Sato | ......................... | G01J 5/16 |
| | | | | 250/338.4 |
| 2008/0137709 A1* | 6/2008 | Quinn | .................. | G01J 5/0025 |
| | | | | 374/121 |
| 2009/0187115 A1* | 7/2009 | Yarden | .................. | G01K 13/20 |
| | | | | 600/549 |

(Continued)

FOREIGN PATENT DOCUMENTS

| JP | S63-58223 A | 3/1988 |
|---|---|---|
| WO | 2011/012386 A1 | 2/2011 |

*Primary Examiner* — Mirellys Jagan
(74) *Attorney, Agent, or Firm* — Manabu Kanesaka

(57) ABSTRACT

A biological data measurement device according to the present invention includes a substrate disposed at a position spaced a predetermined distance from a body surface BS of a living organism as a measuring object via a support member so that an air layer is formed between the substrate and the body surface, in which the substrate is provided with a thermometer including an infrared thermometer for measuring a body surface temperature and a substrate thermometer for measuring a substrate temperature, thereby measuring a deep body temperature with higher accuracy.

15 Claims, 34 Drawing Sheets

(56) References Cited

U.S. PATENT DOCUMENTS

| | | | |
|---|---|---|---|
| 2011/0106484 A1* | 5/2011 | Quinn | G01J 5/0275 |
| | | | 702/135 |
| 2013/0053654 A1* | 2/2013 | Caduff | A61B 5/1455 |
| | | | 600/301 |
| 2016/0238463 A1 | 8/2016 | Bieberich et al. | |
| 2016/0256055 A1* | 9/2016 | Okamura | G01J 5/048 |
| 2018/0168505 A1* | 6/2018 | Kawai | A61B 5/4266 |
| 2018/0188114 A1* | 7/2018 | Ou Yang | A61B 5/01 |
| 2019/0175096 A1* | 6/2019 | Xi | A61B 5/01 |
| 2020/0178906 A1* | 6/2020 | Bevan | A61B 5/1032 |
| 2020/0271824 A1* | 8/2020 | Shimuta | G01V 8/20 |

* cited by examiner

|  | THERMAL RESISTIVITY (m·k/W) | THICKNESS (mm) | THERMAL RESISTANCE (m^2·k/W) |
|---|---|---|---|
| FROM CORE TO EPIDERMIS | 5.9 | 25 | 0.15 |
| STATIONARY ATMOSPHERE | 40 | 3 | 0.12 |
| WINTER CLOTHING | AIR 40<br>UNDERWEAR 20<br>SHIRTS 20<br>SWEATER 25 | 3<br>1<br>1<br>3 | 0.24 |
| OPEN ATMOSPHERE |  |  | 0.05 |

|  | THERMAL RESISTIVITY (m·k/W) | THICKNESS (mm) | THERMAL RESISTANCE (m^2·k/W) |
|---|---|---|---|
| FROM CORE TO EPIDERMIS | 5.9 | 25 | 0.15 |
| STATIONARY ATMOSPHERE | 40 | 3 | 0.12 |
| SUMMER CLOTHING | AIR 40<br>SHIRTS 20 | 1<br>1 | 0.059 |
| OPEN ATMOSPHERE |  |  | 0.05 |

|  | THERMAL RESISTIVITY (m·k/W) | THICKNESS (mm) | THERMAL RESISTANCE (m^2·k/W) |
|---|---|---|---|
| FROM CORE TO EPIDERMIS | 5.9 | 25 | 0.15 |
| STATIONARY ATMOSPHERE | 40 | 3 | 0.12 |
| POLYSTYRENE | 8 | 3 | 0.024 |
| SUMMER CLOTHING | AIR 40<br>SHIRTS 20 | 1<br>1 | 0.059 |
| OPEN ATMOSPHERE |  |  | 0.05 |

11,12,17,18 : TEMPERATURE SENSOR

BIOLOGICAL DATA MEASUREMENT DEVICE

RELATED APPLICATIONS

The present application is based on, and claims priority from, Japanese Application No. JP2017-231112 filed Nov. 30, 2017, the disclosure of which is hereby incorporated by reference herein in its entirety.

TECHNICAL FIELD

The present invention relates to an object data measurement device, especially a biological data measurement data device attached onto a body surface of a living organism to measure biological data. In particular, the present invention relates to a biological data measurement device for measuring especially a deep body temperature of the living organism.

BACKGROUND

At the present time, a single-heat-flux (SHF) method, a dual-heat-flux (DHF) method, and a zero-heat-flux (ZHF) method are known as a method for measuring a deep body temperature by attaching a device onto a body surface of a living organism.

FIG. 29 shows a configuration of FIG. 2 described in Patent Reference 1 (WO 2011/012386A) as one example of the single-heat-flux (SHF) method. In FIG. 29, a reference number 2 indicates a first probe, 6 indicates a second probe, 4 indicates a heat insulating material, and 3 indicates a body surface. A heat flow (heat flux) generated substantially perpendicular to the body surface 3 is measured by the first probe 2 and the second probe 6.

The SHF method has advantages that a heater is not required and thus a simple configuration is advantageously implemented with a lower power consumption, but has a disadvantage that the measurement is likely to take about 10 minutes. Additionally, it is necessary to measure a thermal resistance (in vivo thermal resistance) in the living organism by another method in advance.

FIG. 30 shows a configuration of FIG. 1 described in Patent Reference 2 (JP S63-058223 A) as one example of the dual-heat-flux (DHF) method. In FIG. 30, reference numbers 11 and 17 indicate a pair of first temperature sensors, while 12 and 18 indicate a pair of second temperature sensors. A deep body temperature of a living organism is measured based on a heat flow measured by the pair of first temperature sensors 11, 17 and a heat flow measured by the pair of the second temperature sensors 12, 18.

The DHF method has advantageous effects that the deep body temperature can be acquired without measuring an in vivo thermal resistance by another method, and a heater is not required and thus the power consumption is low. However, the measurement also takes about 10 minutes, and two pairs of temperature sensors are needed.

FIG. 31 shows a configuration of FIG. 6 described in Patent Reference 3 (US 2016/0238463 A) as one example of the zero-heat-flux (ZHF) method. In FIG. 31, a reference number 140 indicates a temperature sensor, and 126 indicates a heater.

According to the ZHF method, the temperature sensor 140 affixed onto a skin surface is heated by the heater 126, and a deep body temperature is displayed on a display when the temperature sensor 140 and the deep body temperature reach equilibrium (it takes about 3 minutes).

As described above, the ZHF method has an advantage that the measurement takes a relatively short time, e.g. about 3 minutes, but on the other hand, has a disadvantage that the power consumption of the heater is about 1 W (watt).

Since the ZHF method needs the power consumption of about 1 W, it is difficult to apply the ZHF method to a bandage-type sensor used by being adhered to the body surface.

Regarding wirings around the sensor, four wirings are required even for the SHF method, while eight wirings are required for the DHF method. These wirings are needed to be connected to a single reading circuit or the like, thus it takes a lot of trouble.

Heat conduction in a horizontal direction (a direction substantially parallel to the body surface) by the wiring causes sensitivity deterioration and device faults. Furthermore, the device is connected to data collection equipment via the wiring, thus it takes time to attach the device onto the living organism and wearing device is a kind of burden.

Moreover, the SHF method has advantages that a heater is not required and thus a simple configuration is advantageously implemented with a lower power consumption, but has a disadvantage that it is necessary to measure a thermal resistance (in vivo thermal resistance) in the living organism by another method in advance.

SUMMARY

A first object of the present invention is to provide a biological data measurement device which has a simple configuration, excellent wearability to a body surface of a living organism, and is capable of accurately measuring, in particular, a deep body temperature.

A second object of the present invention is to provide a measurement device, in particular, a biological data measurement device which adopts the SHF method as having a single temperature measurement unit, and is capable of obtaining a deep body temperature without measuring an in vivo thermal resistance of a measuring object by another unit.

The present invention includes a first invention for achieving the first object and a second invention for achieving the second object.

For achieving the first object, a biological data measurement device according to the first invention, includes a substrate disposed at a position spaced a predetermined distance from a body surface of a living organism as a measuring object via a support member so that an air layer is formed between the substrate and the body surface. The substrate is provided with a thermometer including an infrared thermometer for measuring a body surface temperature of the body surface and a substrate thermometer for measuring a substrate temperature of the substrate.

It is preferable that the infrared thermometer is provided with a calibration thermometer, and the calibration thermometer is used for the substrate thermometer.

The support member is made of a heat insulating material and forms a substantially sealed space as the air layer between the infrared thermometer and the body surface. It is preferable that a foamed plastic material is used as the heat insulating material.

It preferable that the infrared thermometer is provided on a lower surface side of the substrate, opposing to the body surface, and the substrate is the covered with the heat insulating material at a portion other than the air layer, including an upper surface thereof.

In another aspect, the infrared thermometer may be provided on a lower surface side of the substrate, opposing to the body surface, and the heat insulating material may be disposed as a cylindrical body on the lower surface side of the substrate so as to surround the air layer.

In the first invention, the substrate is provided with a transmitter which wirelessly transmits a body surface temperature measured by the infrared thermometer and a substrate temperature measured by the substrate thermometer.

As the substrate is provided with the transmitter, the substrate is accommodated in a case at least partially having an electromagnetic wave transmission region in a state where the substrate is supported by the heat-insulating material.

In the first invention, the case may include a box body of which a bottom surface on a body surface side is open, and which has a top plate and a side plate bent downward at a substantially right angle from a peripheral edge of the top plate, the bottom surface may be entirely covered with a sheet, and an adhesive gel may be applied on a body surface side of the sheet.

The sheet and the adhesive gel may be made of an infrared-transparent material.

In the first invention, the case may be provided with a box-shaped case body of which a top surface is open and which has a bottom plate and a side plate bent upward at a substantially right angle from a peripheral edge of the bottom plate; and a lid which detachably covers the top surface of the case body.

In the first invention, a high thermal conductive film is provided in the case in order to transmit heat entering into and leaving from a side plate side.

The biological data measurement device according to the first invention includes a calculator. When the body surface temperature is Tsk, the substrate temperature is Tsub, a thermal resistance of the air layer is Rthair, and a heat flow that flows substantially perpendicular to the body surface is Ith, the calculator obtains the heat flow Ith from an equation (Tsk−Tsub)/Rthair.

When a thermal resistance from a deep tissue to the body surface in the living organism is Rthbody and a deep body temperature of the living organism is Tcore, the calculator obtains the deep body temperature Tcore from an equation Tsk+Ith×Rthbody.

In the first invention, the biological data measurement device may include in vivo electrical resistance measurement means for measuring an electrical resistance in the living organism. The thermal resistance Rthbody may be estimated from an in vivo electrical resistance value measured by the in vivo electrical resistance measurement means.

In the biological data measurement device according to another aspect, a first thermometer and a second thermometer are disposed in parallel on the substrate, as the thermometer. The first thermometer includes a first infrared thermometer for measuring a body surface temperature of the body surface and a first substrate thermometer for measuring a substrate temperature of the substrate. The second thermometer includes a second infrared thermometer for measuring a body surface temperature of the body surface and a second substrate thermometer for measuring a substrate temperature of the substrate. The upper surface of the substrate, on which the first thermometer is disposed, is covered with the heat insulating material.

The biological data measurement device according to another aspect includes a calculator for obtaining a deep body temperature Tcore of the living organism. When the body surface temperature measured by the first thermometer is Tsk1, a heat flow that flows substantially perpendicular to the body surface is Ith1, the body surface temperature measured by the second thermometer is Tsk2, a heat flow that flows substantially perpendicular to the body surface is Ith2, a thermal resistance from a deep tissue to the body surface in the living organism is Rthbody, the calculator calculates Rthbody from an equation (Tsk2−Tsk1)/(Ith1−Ith2) and then obtains the deep body temperature Tcore of the living organism from an equation (Ith1×Rthbody+Tsk1) or (Ith2×Rthbody+Tsk2).

For achieving the second object, the second invention encompasses several aspects as described below.

In an object data measurement device according to a first aspect of the second invention, an object having a first thermal resistance Rth1 from a core to a surface is a measuring object. The object data measurement device includes a heat insulating layer which is disposed on a body surface of the measuring object and has a second thermal resistance Rth2; measurement means for measuring a first and a second temperatures, which is segregated by the heat insulating layer; calculation means for calculating the first thermal resistance based on the first and the second temperatures measured at a first timing A, and the first and the second temperatures measured at a second timing B after a predetermined time has elapsed from the first timing A; and calculation means for calculating a deep body temperature of the measuring object based on the first and the second thermal resistances, and the first and the second temperatures.

According to a second aspect of the second invention, the object data measurement device includes calculation means for calculating the first thermal resistance Rth1 from an equation Rth2×b/(a−b) when a difference between the first temperatures measured at the first timing A and measured at the second timing B is a, a difference between the second temperatures measured at the first timing A and measured at the second timing B is b, and the second thermal resistance is Rth2.

According to a third aspect of the second invention, the object data measurement device includes calculation/change means for calculating a deep body temperature TcoreA of the measuring object at the first timing A and a deep body temperature TcoreB of the measuring object at the second timing B based on a temporary value set as the first thermal resistance Rth1, and for changing a value of the first thermal resistance Rth1 so that an absolute value obtained by subtracting the deep body temperature TcoreB from the deep body temperature TcoreA falls within a predetermined determination value range.

According to a fourth aspect of the second invention, the first temperature is a bottom side temperature of a bottom surface of the heat insulating layer, which is in contact with an object surface, the second temperature is a top side temperature of a top surface of the heat insulating layer, and the object data measurement device further includes adding means for adding a predetermined delay time to the second temperature in order to correct a response delay of the first temperature as compared with the second temperature.

According to a fifth aspect of the second invention, a biological data measurement device includes a substrate disposed at a position spaced a predetermined distance from a body surface of a living organism as a measuring object via a support member so that an air layer is formed between the substrate and the body surface. The substrate is provided with temperature measurement means including an infrared thermometer for measuring a body surface temperature Tsk of the body surface and a substrate thermometer for measuring a substrate temperature Tsub of the substrate, and the temperature measurement means measures the body surface temperature Tsk and the substrate temperature Tsub in the same place at least twice, that is, at a first timing A and a second timing B.

According to a sixth aspect of the second invention, an in vivo thermal resistance Rthbody is calculated from an equation Rthair×b/(a−b) when a difference between the body surface temperatures Tsk measured at the first timing A and measured at the second timing B is a, a difference between the substrate temperatures Tsub measured at the first timing A and measured at the second timing B is b, and a thermal resistance of the air layer is Rthair.

According to a seventh aspect of the second invention, when a thermal resistance of the air layer is Rthair and a heat flow that flows substantially perpendicular to the body surface is Ith, the heat flow Ith is obtained from an equation (Tsk−Tsub)/Rthair, and a predetermined delay time is added to the substrate temperature Tsub in order to correct a response delay of the body surface temperature Tsk as compared with the substrate temperature Tsub.

According to an eighth aspect of the second invention, the deep body temperature TcoreA at the first timing A is compared with the deep body temperature TcoreB at the second timing B, both of which are calculated based on a heat flow IthA measured at the first timing A after the biological data measurement device is wore on the body surface, a heat flow IthB measured at the second timing B after a predetermined time has elapsed from the first timing A, and a temporary value set in advance as the in vivo thermal resistance Rthbody. A value of the in vivo thermal resistance Rthbody is corrected so that an absolute value obtained by subtracting the deep body temperature TcoreB from the deep body temperature TcoreA falls within a predetermined determination value range.

According to a ninth aspect of the second invention, a ZHF state is temporarily created by raising a case temperature Tcase of a case, in which the biological data measurement device is accommodated, up to a deep body temperature Tcore using a heating element, thereby calculating the in vivo thermal resistance Rthbody based on the ZHF state.

According to a tenth aspect of the second invention, the case is provided with calibration means for subjecting to a calibration by the heating element.

According to an eleventh aspect of the second invention, the biological data measurement device includes a step of instructing to remove the heating element from the case when the case temperature Tcase exceeds a predetermined temperature Tth.

According to a twelfth aspect of the second invention, a step of obtaining the in vivo thermal resistance Rthbody is executed when an environmental temperature changes at a rate at which the deep body temperature Tcore does not significantly change.

According to a thirteenth aspect of the second invention, a step of obtaining the in vivo thermal resistance Rthbody is executed when a heart rate of the living organism as the measuring object is equal to or less than a predetermined threshold value.

According to a fourteenth aspect of the second invention, a step of obtaining the in vivo thermal resistance Rthbody is executed when a temporary in vivo thermal resistance Rthbody is obtained by multiplying an in vivo body core distance body_d from a body core to a body surface by a thermal resistivity from the body core to the body surface.

According to a fifteenth aspect of the second invention, the in vivo thermal resistance Rthbody is calculated back from the substrate temperature Tsub and the body surface temperature Tsk, both of which are obtained at an initial stage of the measurement, so that the deep body temperature Tcore becomes a body temperature at rest which is input in advance.

According to a sixteenth aspect of the second invention, an ECG measurement circuit for measuring electrocardiogram is mounted on the substrate. A wearing belt for wearing a case of the biological data measurement device on the body surface is provided. At least two electrodes in contact with the body surface are disposed at a predetermined distance apart on the wearing belt. A contact portion is provided between the wearing belt and the case in order to connect the two electrodes to the ECG measurement circuit. A body temperature signal measurement by the temperature measurement means is carried out simultaneously with an electrocardiographic signal measurement by the ECG measurement circuit.

In a biological data measurement device according to a seventeenth aspect of the second invention, a living organism having a first thermal resistance Rth1 from a core to a surface is a measuring object. The biological data measurement device includes a heat insulating layer which is disposed on a surface of the measuring object and has a second thermal resistance Rth2; measurement means for measuring a first and a second temperatures, which is segregated by the heat insulating layer; and adding means for adding a predetermined delay time to the second temperature in order to correct a response delay of the first temperature as compared with the second temperature. The first temperature is a bottom side temperature of a bottom surface of the heat insulating layer, which is in contact with the body surface, and the second temperature is a top side temperature of a top surface of the heat insulating layer.

According to the first invention, the infrared thermometer and the substrate thermometer are provided on the substrate disposed at a position spaced the predetermined distance from the body surface via the support member (heat insulating material), thus it is possible to easily manufacture the biological data measurement device with a low cost. Moreover, since the heat insulating layer between the substrate and the body surface is the air layer, the thermal resistance between the substrate and the body surface can be increased.

The heat insulating material serving as the support member forms the space between the infrared thermometer and the body surface, thus error on the ambient temperature can be reduced.

Since the biological data measurement device includes the transmitter which wirelessly transmits a body surface temperature measured by the infrared thermometer and a substrate temperature measured by the substrate thermometer, the heat transfer through the wiring of the wired transmitter does not occur, and thus the deep body temperature can be measured with higher accuracy.

The first thermometer and the second thermometer are disposed in parallel on the substrate. The first thermometer includes a first infrared thermometer for measuring a body surface temperature of the body surface and a first substrate thermometer for measuring a substrate temperature of the substrate. The second thermometer includes a second infrared thermometer for measuring a body surface temperature of the body surface and a second substrate thermometer for measuring a substrate temperature of the substrate. The upper surface of the substrate, on which the first thermometer is disposed, is covered with the heat insulating material.

Therefore, the deep body temperature can be measured without measuring the in vivo thermal resistance by another method.

According to the second invention, when a difference between the first temperatures measured at the first timing A and measured at the second timing B is a, a difference between the second temperatures measured at the first timing A and measured at the second timing B is b, and the second thermal resistance is Rth2 (already known), the first thermal resistance (in vivo thermal resistance of the measuring object) Rth1 can be calculated from the equation Rth2×b/(a−b). Therefore, the SHF method is adopted as having a single temperature measurement unit, and the deep body temperature can be obtained without measuring the in vivo thermal resistance of the measuring object by another unit.

As described above, two heat flows are measured in the same place at the timing A and the timing B, which are temporally away from each other, using the same thermometer. Consequently, it is hardly influenced by variation due to place or thermometer. Furthermore, the biological data measurement device can be downsized with the significantly reduced power consumption, as compared with those employing the DHF or ZHF method.

DESCRIPTION OF THE EMBODIMENTS

Some embodiment according to the present invention will be described with reference to FIGS. 1 to 28. However, the present invention is not limited to these embodiments.

Figure 1A:
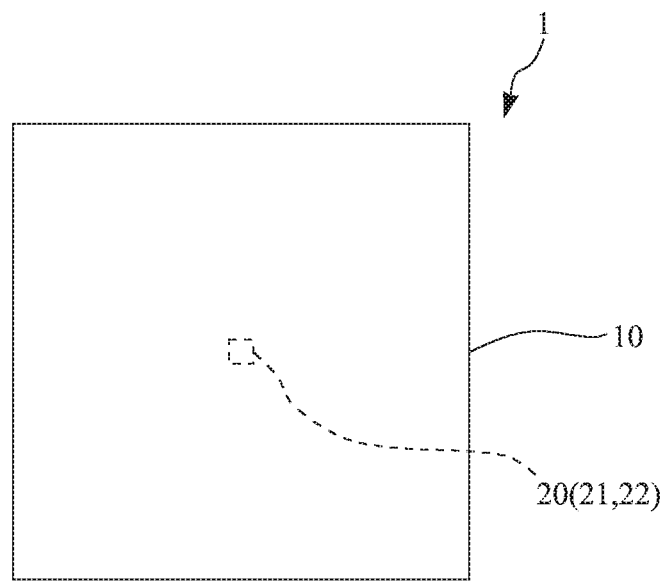
FIG. 1(a) shows a schematic plan view and FIG. 1(b) shows a schematic cross-sectional view thereof, both illustrating a basic aspect (first embodiment) of the present invention.
Figure 1B:
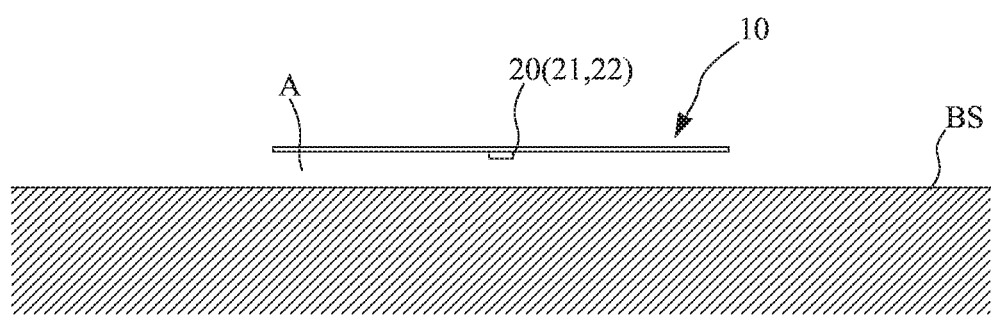

First, referring to FIG. 1, a biological data measurement device 1 of the present invention includes a substrate 10 provided with a thermometer (temperature measurement means) 20 as a basic form (first embodiment). The substrate 10 is disposed at a position spaced a predetermined distance from a body surface BS of a living organism as a measuring object via a support member (described later) (for example, at a position spaced about 3 mm from the body surface BS).

The substrate 10 is, for example, a polyimide substrate. It is preferable to set a thickness of the substrate 10 to about several hundred microns to reduce the heat capacity. It is also preferable that the substrate 10 is in a shape of a square of 30 mm$^2$ or more. However, the substrate 10 may be a circle or a polygon other than a square, having substantially the same area.

Although not shown in detail, the thermometer 20, corresponding to the temperature measurement means, includes an infrared thermometer 21 for measuring a temperature Tsk of the body surface BS, and a substrate thermometer 22 for measuring a substrate temperature Tsub of the substrate 10. The infrared thermometer 21 is disposed on a lower surface side of the substrate 10 so as to face the body surface BS. A hole may be formed in the substrate 10, and the infrared thermometer 21 may be mounted in the hole.

A bolometer detector, a thermopile detector or the like is used as the infrared thermometer 21 to measure an amount of infrared radiation of the body surface BS. The substrate thermometer 22 is a thermometer for measuring the substrate temperature Tsub of the substrate 10. The substrate thermometer 22 may be provided separately from the infrared thermometer 21; however, a calibration thermometer equipped with the infrared thermometer 21 may be used as the substrate thermometer 22.

When a thermal resistance of an air layer A between the substrate 10 and the body surface BS is Rthair, a heat flow (heat flux) Ith that flows substantially perpendicular to the body surface BS can be obtained from the equation (Tsk−Tsub)/Rthair.

A thermal resistance Rth between the substrate 10 and body surface BS can be increased by forming the air layer A. However, a solid heat insulating layer made of, for example, a foam material or the like may be adopted instead of the air layer A. In this case, a thermometer for measuring the body surface temperature is provided on surface on a body surface side of the solid heat insulating layer, instead of the infrared thermometer.

When a deep body temperature of the living organism is Tcore, and a thermal resistance from a deep tissue to the body surface BS in the living organism is Rthbody, the deep body temperature Tcore can be obtained from the equation Tsk+Ith×Rthbody.

In the first embodiment, the in vivo thermal resistance Rthbody is measured by another method (not shown). As one example of another method, the in vivo thermal resistance Rthbody is measured from an in vivo electrical resistivity measured by in vivo electrical resistivity measurement means, which measures the in vivo electrical resistivity (Galvanic skin resistance, GSR) by flowing a weak electric current (for example, about 0.2 μA) to the living organism with a pair of electrodes. The present invention also encompasses an embodiment including the in vivo electrical resistivity measurement means.

Figure 2A:
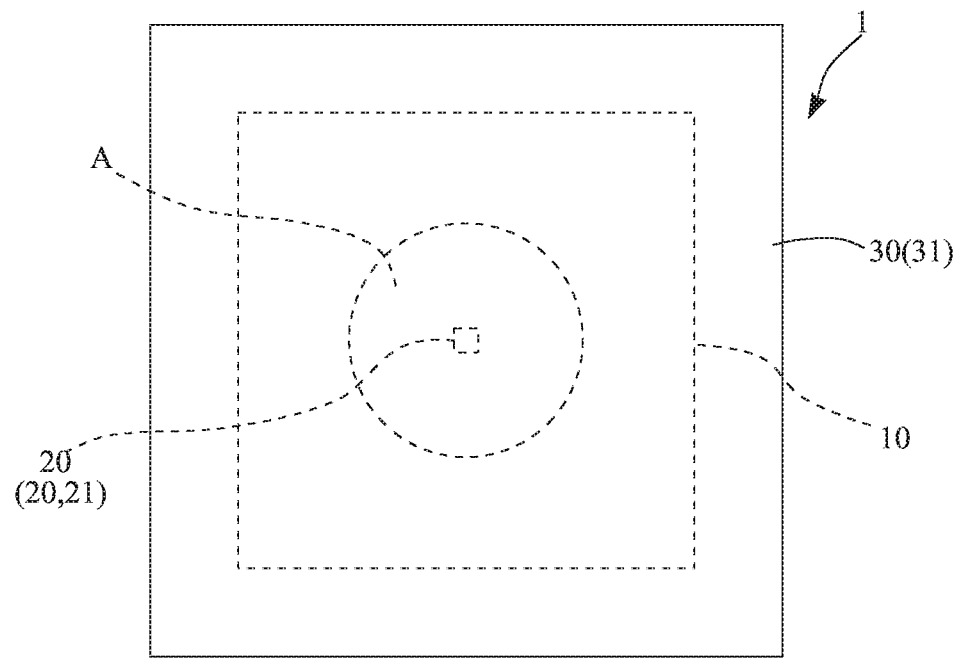
FIG. 2(a) shows a schematic plan view and FIG. 2(b) shows a cross-sectional view thereof, both illustrating a second embodiment of the present invention.
Figure 2B:
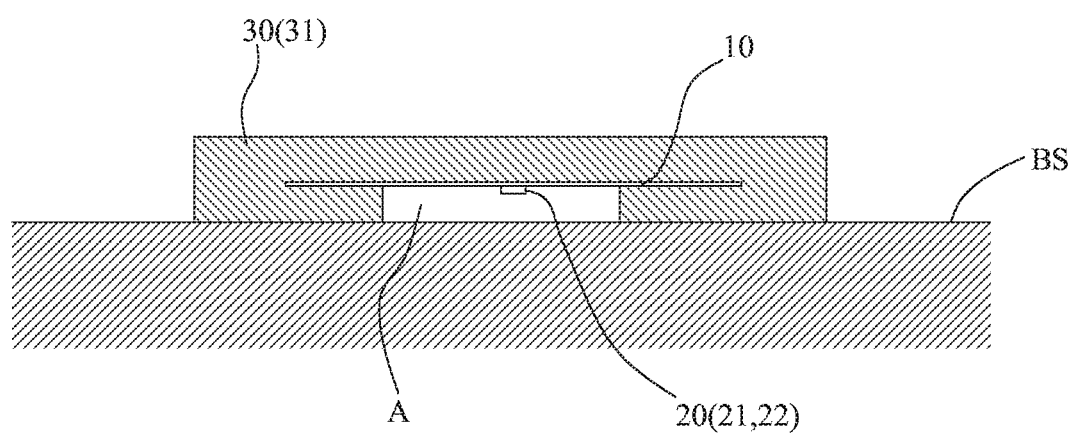

Referring to FIG. 2, the biological data measurement device 1 according to a second embodiment is provided with a support member 30 that supports the substrate 10 at a predetermined height position on the body surface BS. The support member 30 preferably employs a heat insulating material 31, e.g. a foamed plastic material or the like, which has the thermal resistance Rth as large as possible, and is hardly deformed by external force.

Examples of the foamed plastic material include polyurethane, polystyrene, and the like. Rigid urethane foam made of polyurethane has a thermal resistivity equivalent to 40 m·K/W at the stationary atmosphere. A compressive strength of several hundred gf/cm$^2$ to 1 kgf/cm$^2$ can be produced.

In this embodiment, the support member 30 (heat insulating material 31) forms a substantially sealed space as the air layer A between the infrared thermometer 21 and the body surface BS when attaching onto the body surface BS, and covers the substrate surface including an upper surface, other than the air layer.

Figure 3A:
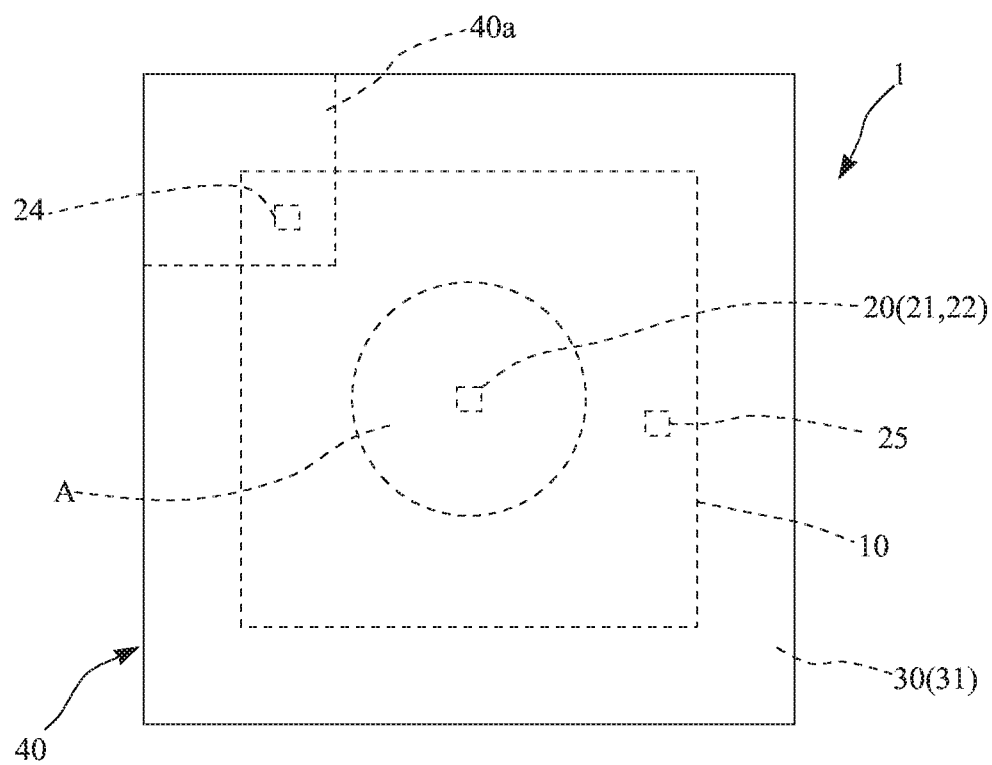
FIG. 3(a) shows a schematic plan view and FIG. 3(b) shows a cross-sectional view thereof, both illustrating a third embodiment of the present invention.
Figure 3B:
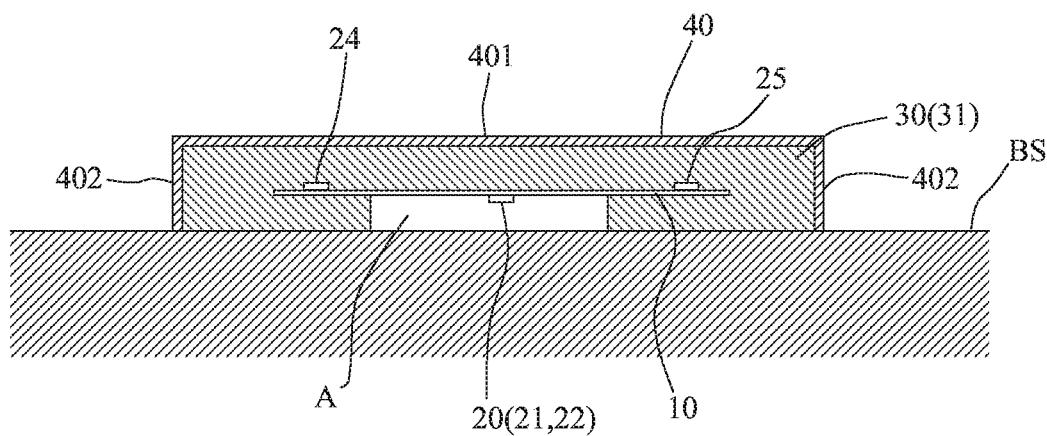

In a third embodiment shown in FIG. 3, the biological data measurement device 1 is provided with a case 40 for reducing the lateral release of a heat flow Ith from the body surface BS. The case 40 includes a box body of which a bottom surface (surface on a body surface BS side) is open, and which has a top plate 401 and a side plate 402 bent downward at a substantially right angle from a peripheral edge of the top plate 401. The substrate 10 is accommodated in the case 40 while being supported by the heat insulating material 31.

On the other hand, in the third embodiment, the substrate 10 is provided with a transmitter 24 and a calculator 25. The calculator 25 calculates the heat flow Ith from the body surface temperature Tsk measured by the infrared thermometer 21, the substrate temperature Tsub measured by the substrate thermometer 22, and the thermal resistance Rthair of the air layer A, as described above as one example. The transmitter 24 wirelessly transmits the calculated values to a data collection/analysis device as a parent device (not shown).

A wireless module or the like is used as the transmitter 24, and a microcomputer or the like is used as the calculator 25. In a case where these modules or packages include a heat generation component, of which heat (in many cases, minute heat) causes faults in the measurement of the deep body measurement, the transmitter 24 and/or the calculator 25 can be disposed outside the case 40 as one of countermeasures.

As another method, a high thermal conductive material for improving the heat conduction of the body surface BS with the transmitter 24 and/or the calculator 25 may be provided on the air layer A (for example, a lower surface of the substrate 10) to release the heat generated by the transmitter 24 and/or the calculator 25 to the body surface BS.

Furthermore, the transmitter 24 and/or the calculator 25 may be provided on an upper surface of the substrate 10 to release the heat to the atmosphere, or a heat insulator may be interposed between the transmitter 24 and/or the calculator 25 and the thermometer 20.

As another aspect, the calculator 25 may be provided on the parent device (data collection/analysis device) side, and the transmitter 24 may transmit data including the body surface temperature Tsk and the substrate temperature Tsub to the parent device, thereby obtaining the heat flow Ith and the deep body temperature Tcore on the parent device side. This aspect is also encompassed in the present invention.

It is preferable that the case 40 is made of a material that reduces the temperature distribution in a horizontal direction and is transmissive to the radio wave (electromagnetic wave) of the transmitter 24. An exemplified material is alumina. In addition, the thermal resistivity of alumina is 0.03 m·K/W.

A patterned printed circuit board can also be used instead of alumina. In this case, a conductor (copper foil) is excluded from a specific portion 40a (an upper right corner in FIG. 3(a)) of the transmitter 24, corresponding to a communication antenna so that the radio wave can pass. The side plate 402 of the case 40 may be made of metal.

The transmitter 24 can use a radio band of 2.4 GHz or 13.56 MHz (industrial, scientific and medical radio bands). Although not shown, the substrate 10 is provided with a battery (preferably a secondary battery) for supplying power to the transmitter 24 and/or the calculator 25. However, the power may be supplied from the parent device side at 13.56 MHz.

Figure 4A:
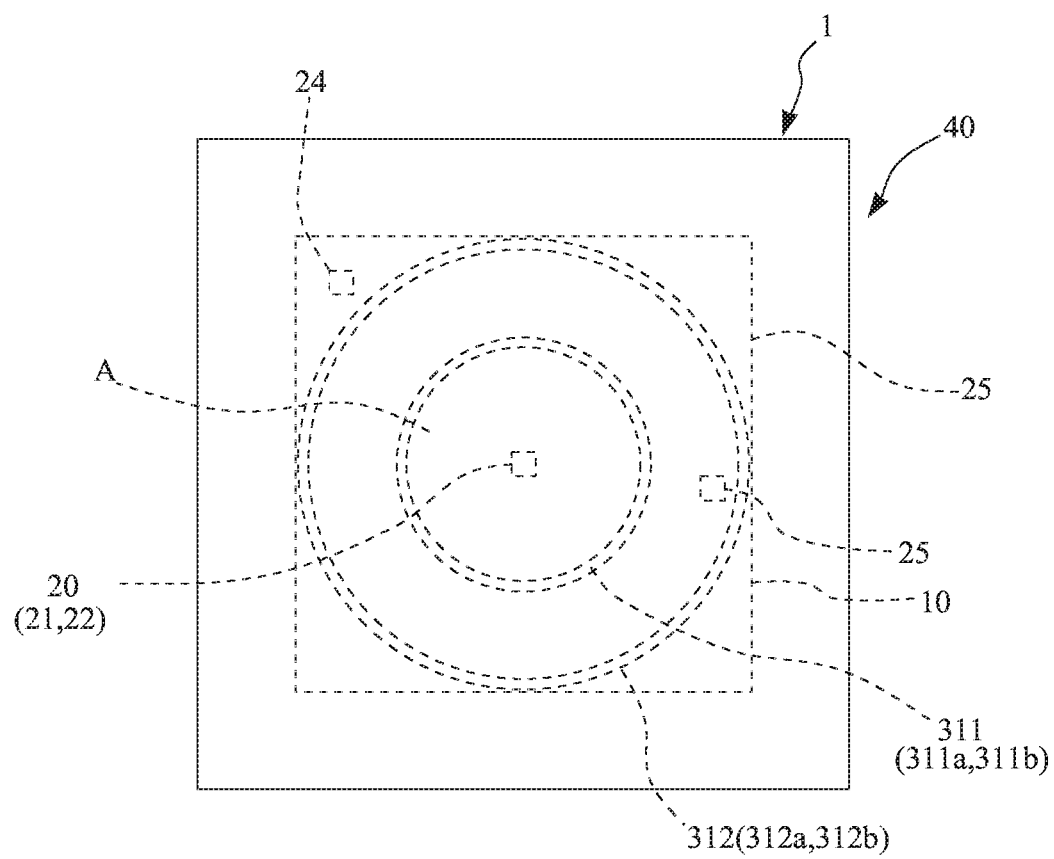
FIG. 4(a) shows a schematic plan view and FIG. 4(b) shows a cross-sectional view thereof, both illustrating a fourth embodiment of the present invention.
Figure 4B:
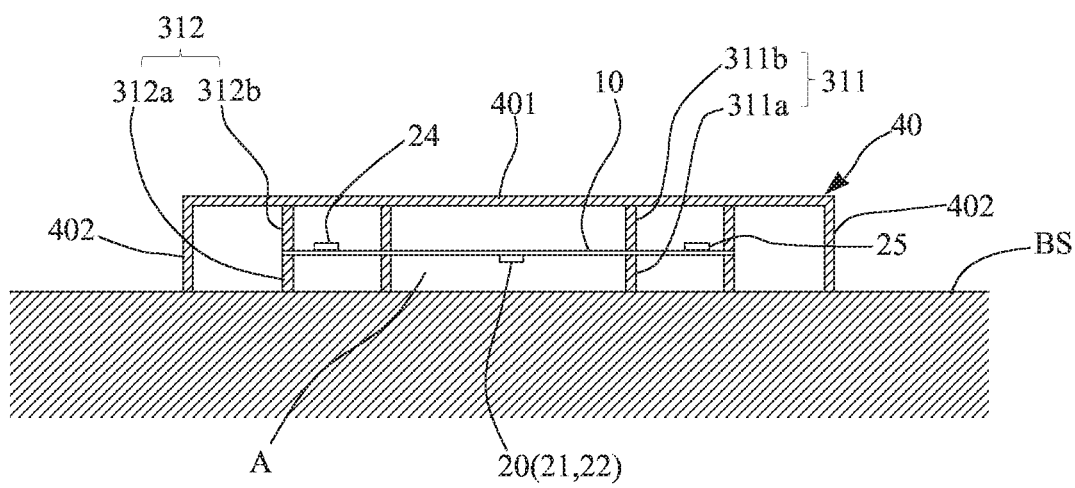

In a fourth embodiment shown in FIG. 4, cylindrical heat insulating materials 311, 312 are used as the support member 30. The heat insulating materials 311, 312 are arranged concentrically. The heat insulating material 311 is on the inside and the heat insulating material 312 is on the outside.

In the fourth embodiment, the inner heat insulating material 311 is provided with a cylindrical lower heat insulating material 311a provided on the lower surface side of the substrate 10 to form a sealed space (air layer A) between the infrared thermometer 21 and the body surface BS when attaching onto the body surface BS, and an upper heat insulating material 311b disposed between the upper surface of the substrate 10 and an inner surface of the case 40.

The outer heat insulating material 312 is a support member for supporting an outer peripheral side of the substrate 10, and is provided with a cylindrical lower heat insulating material 312a provided on the lower surface side of the substrate 10 and an upper heat insulating material 312b disposed between the upper surface of the substrate 10 and the inner surface of the case 40.

Moreover, in the fourth embodiment, the upper heat insulating material 311b and the lower heat insulating material 311a, included in the inner heat insulating material 311, have the same diameter, but may have different diameters. Similarly, the upper heat insulating material 312b and the lower heat insulating material 312a, included in the outer heat insulating material 312, have the same diameter, but may have different diameters.

In the fourth embodiment, the heat insulating materials 311, 312 are cylindrical, but may be square tubular. Generally, the heat insulating material loses the thermal resistivity as the compressive strength increases, so that the heat resistivity can be increased by adopting the cylindrical heat insulating material. For example, polystyrol has a thermal resistivity of 8 m·K/W. That is, polystyrol has a sufficient strength but a low thermal resistivity, thus it can be partially used.

Figure 5A:
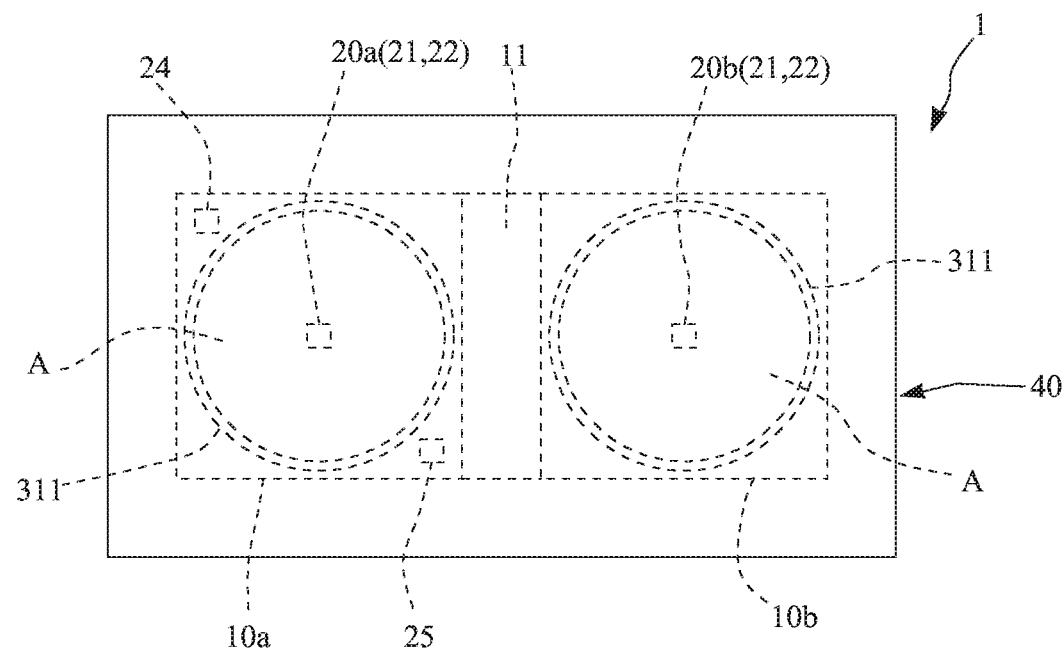
FIG. 5(a) shows a schematic plan view and FIG. 5(b) shows a cross-sectional view thereof, both illustrating a fifth embodiment of the present invention.

Referring to FIG. 5, the biological data measurement device 1 according to a fifth embodiment is provided with two thermometers, i.e. a first thermometer 20a and a second thermometer 20b. Both of the thermometers 20a, 20b include the infrared thermometer 21 and the substrate thermometer 22.

Two substrates 10a, 10b are used as the substrate 10 on which the two thermometers 20a, 20b are installed. The first thermometer 20a is provided on one substrate 10a, and the second thermometer 20b is provided on the other substrate 10b. In this embodiment, both of the transmitter 24 and the calculator 25 are disposed on a side of the substrate 10a.

The substrate 10a and the substrate 10b are connected by a flexible substrate 11. The second thermometer 20b is connected to the transmitter 24 and/or the calculator 25 via a wiring in the flexible substrate 11. As another aspect, the thermometers 20a, 20b may be juxtaposed on the same substrate 10.

Figure 5B:
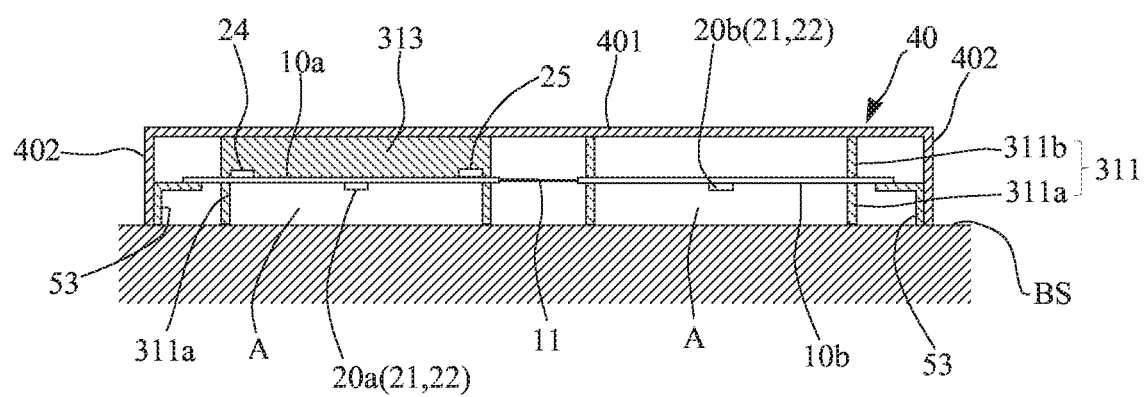

A difference between the thermometers 20a, 20b is that, as shown in FIG. 5(b), a heat insulating material 313 is disposed above one of the thermometers, i.e. the first thermometer 20a, and a space is formed above a side of the second thermometer 20b.

The calculator 25 obtains the deep body temperature Tcore of the living organism based on the body surface temperature Tsk and the substrate temperature Tsub, measured by the thermometers 20a, 20b, as follows.

That is, when a body surface temperature measured by the first thermometer 20a is Tsk1, a heat flow that flows substantially perpendicular to the body surface BS at a portion of the first thermometer 20a is Ith1, a body surface temperature measured by the second thermometer 20b is Tsk2, a heat flow that flows substantially perpendicular to the body surface BS at a portion of the second thermometer 20b is Ith2, and the in vivo thermal resistance from the deep tissue to the body surface BS in the living organism is Rthbody, the calculator 25 calculates Rthbody from the equation (Tsk2−Tsk1)/(Ith1−Ith2), and then obtains the deep body temperature Tcore of the living organism from the equation (Ith1×Rthbody+Tsk1) or (Ith2×Rthbody+Tsk2).

Additionally, when a substrate temperature measured by the substrate thermometer 22 of the first thermometer 20a is Tsub1, a substrate temperature measured by the substrate thermometer 22 of the second thermometer 20b is Tsub2, and the thermal resistance of the air layer A is Rthair, the heat flow Ith1 is obtained from the equation (Tsk1−Tsub1)/Rthair, and heat flow Ith2 is obtained from the equation (Tsk2−Tsub2)/Rthair, as described above.

As described above, according to the fifth embodiment, the in vivo thermal resistance Rthbody from the deep tissue to the body surface BS in the living organism is calculated, thus it is not necessary to measure (estimate) the in vivo thermal resistance Rthbody by another measurement means (for example, the in vivo electrical resistance measurement means, as stated above).

Figure 6A:
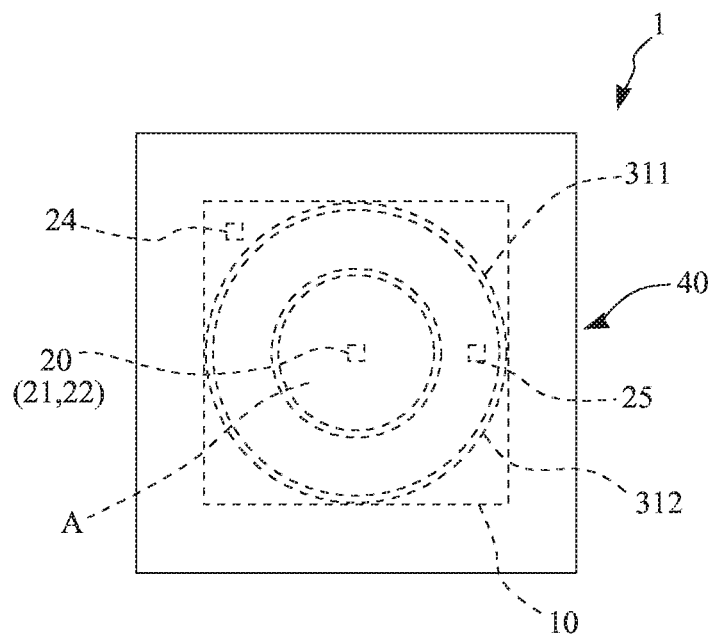
FIG. 6(a) shows a schematic plan view and FIG. 6(b) shows a cross-sectional view thereof, both illustrating a sixth embodiment of the present invention.
Figure 6B:
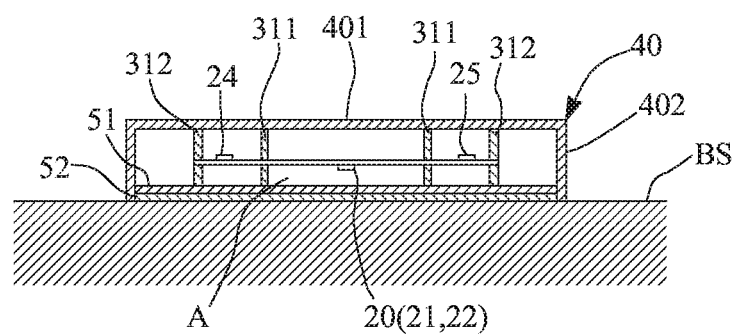

Referring to FIGS. 6(a) and 6(b), the biological data measurement device 1 according to a sixth embodiment is implemented on the basis of, for example, the fourth embodiment shown in FIG. 4, with improved wearability for the living organism.

That is, in the sixth embodiment, an entire lower surface (a surface facing the body surface BS) of the case 40 is covered with a sheet 51, and a lower surface (a surface facing the body surface BS) of the sheet 51 is coated with an adhesive gel 52 with a predetermined thickness, as shown in FIG. 6(b). Accordingly, the biological data measurement device 1 can be smoothly attached onto the body surface BS.

A (highly elastic) material harder than the adhesive gel 52 is used for the sheet 51 in order to prevent the soft adhesive gel 52 from being deformed so that a thickness of the air layer A does not change.

In this case, the infrared thermometer 21 measure a temperature of the sheet 51. The thermal resistance Rth of each of the sheet 51 and the adhesive gel 52 may be subtracted to obtain the in vivo thermal resistance Rthbody. As another method, the body surface temperature Tsk can be measured using an infrared transmissive material in the sheet 51 and the adhesive gel 52.

The thermal resistivity can be increased by enclosing a rare gas such as xenon, kyrton, argon or the like in the space serving as the air layer A. Furthermore, sweat discharge grooves may be formed in the adhesive gel 52 by, for example, subjecting the sheet 51 to the embossing process. Consequently, this embodiment has an advantageous effect of maintaining tackiness of the adhesive gel.

Figure 6C:
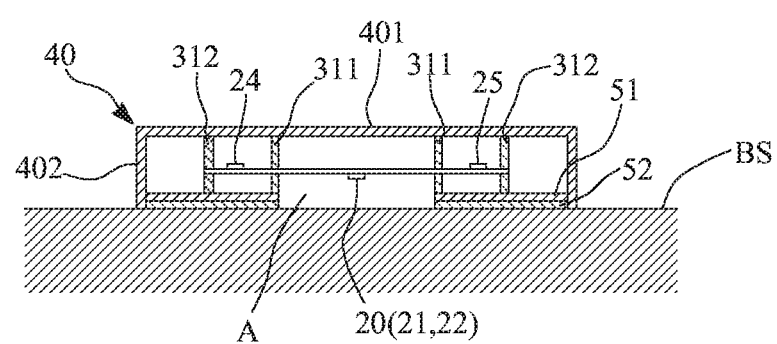
FIG. 6(c) shows a cross-sectional view illustrating a modified example of the fifth embodiment.

As a modified example of the sixth embodiment, the sheet 51 and the adhesive gel 52 may be removed from a center portion of a bottom surface of the case 40, as shown in FIG. 6(c), in order to allow the infrared thermometer 21 to directly measure the body surface temperature. The present invention also encompasses this aspect. A configuration of the sixth embodiment is also applicable to the fifth embodiment illustrated in FIG. 5.

Figure 7A:
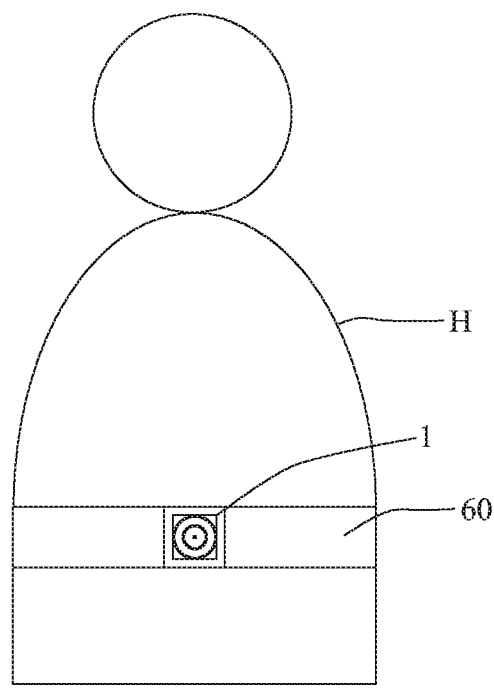
FIG. 7(a) shows a schematic view and FIG. 7(b) shows a cross-sectional view of a main part, both illustrating a state where a biological data measurement device according to the present invention is attached to the living organism using a wearing belt.
Figure 7B:
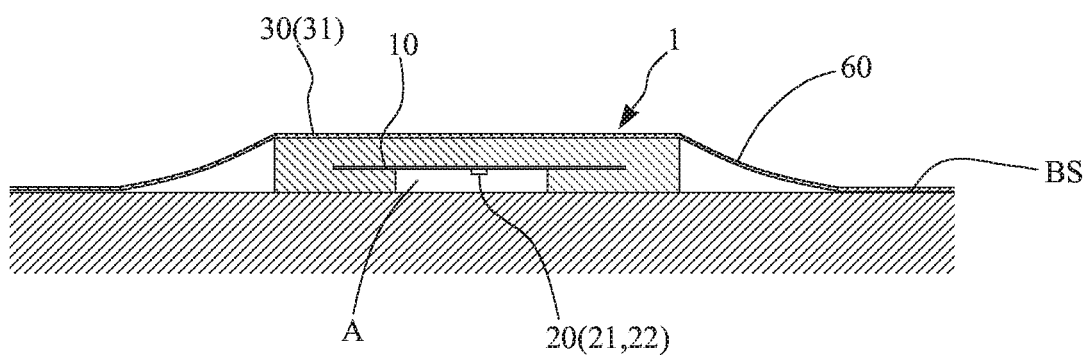
Figure 8A:
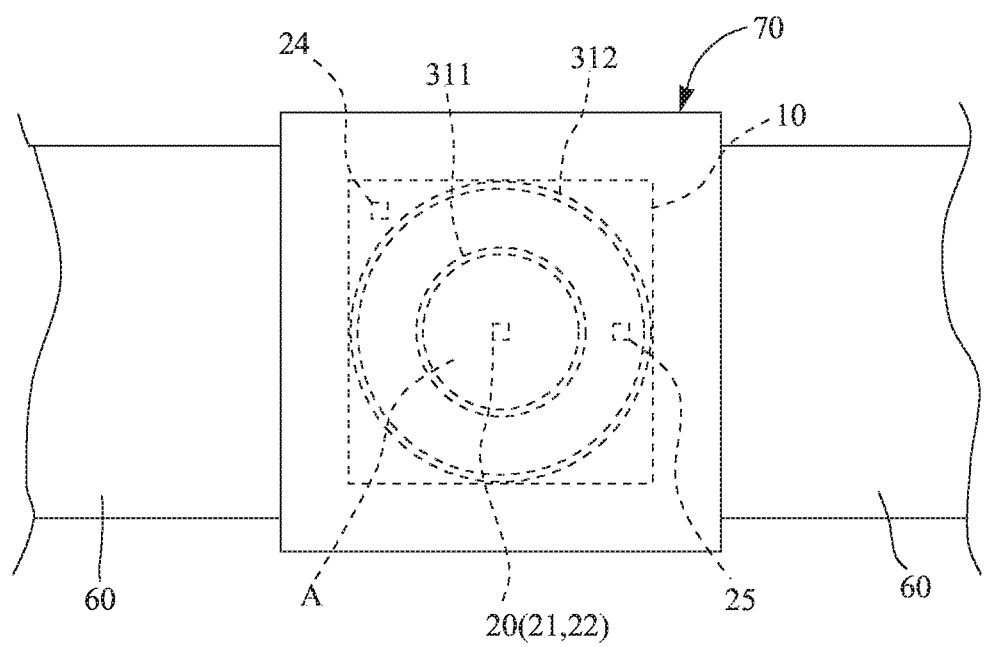
FIG. 8(a) shows a schematic plan view and FIG. 8(b) shows a cross-sectional view thereof, both illustrating a seventh embodiment of the present invention.
Figure 8B:
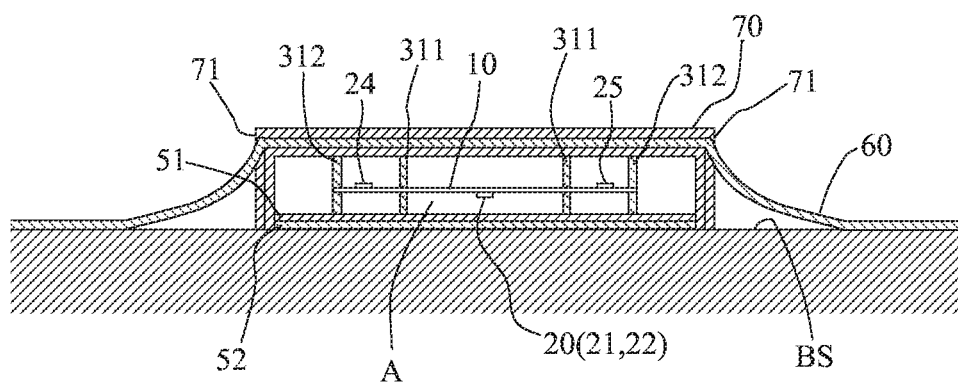

The biological data measurement device 1 is attached to a predetermined region (for example, chest, abdomen, etc.) of a living organism H via a wearing belt 60, as shown in FIGS. 7(a) and 7(b). Furthermore, the biological data measurement device 1 shown in FIG. 7(b) is the biological data measurement device 1 according to the third embodiment illustrated in FIG. 3, but may be the biological data measurement device 1 of another embodiment.

It is preferable that the wearing belt 60 has an elastic structure, and is made of a rubber material having a high elongation rate (preferably a rubber material having an elongation rate of several tens to hundreds %). The wearing belt 60 must not hinder the air permeability to the living organism H, and thus the wearing belt 60 may be a mesh structure for the improved air permeability, as a prevention of heat stroke in the summer.

On the other hand, the case 40 has a low thermal resistance, thus the faults may occur in the measurement of the body temperature due to rapid temperature change when the case 40 is in contact with, for example, an arm, upon attaching to the living organism H. Therefore, in a seventh embodiment shown in FIG. 8, a protective cover 70 for covering the case 40 is provided.

The protective cover 70 is made of a heat insulating material that hardly transmits heat, for example, a highly foamable polyurethane or polystyrene. The protective cover 70 is formed as a box of which a bottom surface larger than the case 40 is open, and is provided with wearing belt insertion openings 71, 71 on opposite side surfaces, through which the wearing belt 60 passes.

Figure 9:
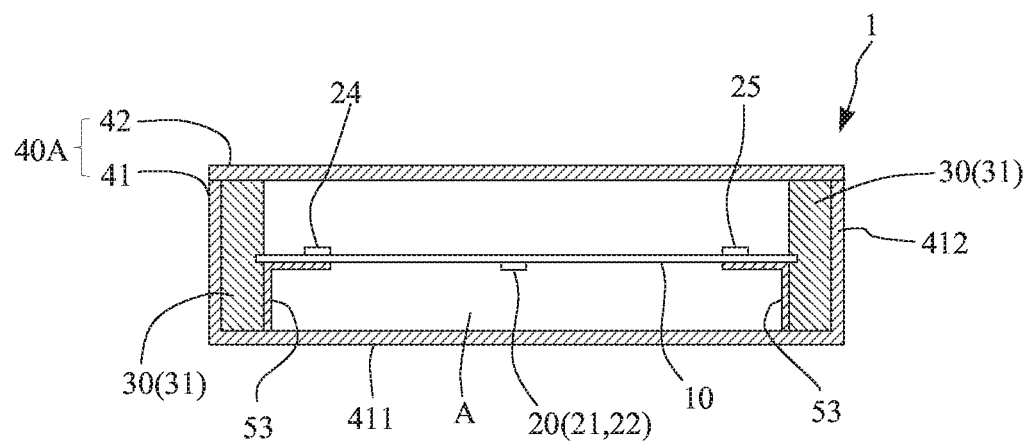
FIG. 9 is a schematic cross-sectional view illustrating an eighth embodiment of the present invention.

An eighth embodiment will be described with reference to FIG. 9. In the eighth embodiment, a case is needed to prevent that the body surfaces BS raises by the fastening force of the wearing belt 60 and a clearance of the air layer A (a distance between the substrate 10 and the body surface BS) changes when the biological data measurement device 1 is attached onto the body surface BS using the wearing belt 60, as stated above. A case 40A is used as such a case, which includes a case body 41 of which a top surface is open and a lid 42 that detachably covers the top surface of the case body 41.

The case body 41 is a box body of which the top surface is open, and which has a square bottom plate 411 and side plates 412 standing on four sides thereof. The substrate 10, provided with the thermometer 20, the transmitter 24, the calculator 25 and the like, is accommodated in the case body 41 while being supported by the heat insulating material 31 as the support member 30. The top surface of the case body 41 is closed with the lid 42 upon using.

In this embodiment, both of the case body 41 and the lid 42 are made of acrylic resin, but other synthetic resin materials may be used as long as they are materials with low thermal resistance and low heat capacity and transmissive to the infrared rays. Moreover, the lid 42 does not need to be a material transmissive to the infrared ray, but needs to be a material transmissive to the radio wave (electromagnetic wave) of the transmitter 24.

The clearance of the air layer A formed between the substrate 10 and the body surface BS is kept to be constant by using such as case 40A even if the biological data measurement device 1 is strongly fastened to the body surface BS with the wearing belt 60.

The biological date measurement device 1 according to the eighth embodiment is provided with a high thermal conductive film 53 for transmitting to the substrate 10 the heat entering into and leaving from a side surface (side plate 412) of the case 40A. The term "high thermal conductive" is defined as having a thermal resistivity of about 0.01 m·K/W (thermal conductivity of about 100 W/m/K). An aluminum foil is preferably used for the high thermal conductive film 53.

According to this embodiment, the high thermal conductive film (aluminum foil) 53 is disposed so as to be in close contact with respective surfaces from lower peripheral edges of the substrate 10 to an inner surface of the heat insulating material 31. Consequently, the body surface temperature (skin temperature) Tsk varies via the substrate 10 even when the environmental temperature changes, thus it is possible to eliminate errors caused by the solely changed body surface temperature Tsk.

It is preferable that the high thermal conductive film 53 has an infrared emissivity close to zero (substantially 0), for the temperature change of the heat insulating material 31 is not radiated toward the air layer A even when the heat cannot be sufficiently transferred to the substrate 10 due to the limited heat conduction.

The high thermal conductive film 53 is applicable to other embodiments including the case 40 of which the bottom surface is open, as illustrated in FIGS. 3 to 6. In this case, the high thermal conductive film 53 is arranged from the side plate 402 to the substrate 10 within the case 40, for example, as shown in FIG. 5(b).

A correlation between the thermal resistance and the temperature in each case when measuring the body temperature will be described with reference to the biological data measurement device 1 according to the fourth embodiment illustrated in FIG. 4.

Figures 10A, 10B:
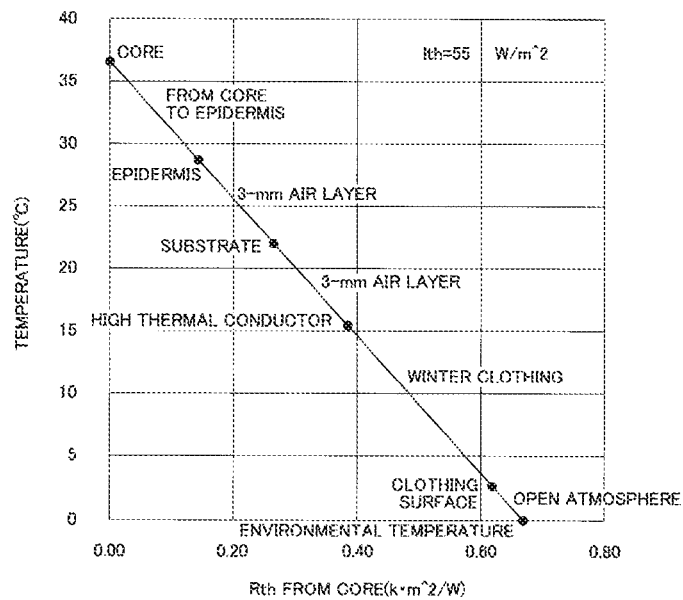
FIG. 10(a) shows a graph illustrating a temperature gradient from a body core to an environmental temperature in the winter.
FIG. 10(b) shows a table illustrating a thermal resistivity, a thickness and a thermal resistance of each case in the wither, in the first to fourth embodiments of the present invention.

A graph shown in FIG. 10(a) indicates a transition of the heat flow (heat flux) in each case in the winter, where a horizontal axis denotes the thermal resistance Rth (K·m²/W) and a vertical axis denotes the temperature (° C.). This graph is drawn assuming that it is the winter season where, for example, the deep body temperature is 36.5° C., the environmental temperature is 0° C., and the user wears underwear, shirts and sweater.

See a table shown in FIG. 10(b) for data on thermal resistivity and thermal of each case, including: a region from the body core to the body surface (assuming that the depth is 25 mm), stationary atmosphere (assuming that 3-mm air layers are formed above and below the substrate, respectively), winter clothing (assuming that 1-mm air layers are formed under the underwear, the shirts and the sweater, respectively), and open atmosphere (with convention).

In the graph of FIG. 10(a), a gradient (T/Rth) of the straight line is the heat flow (heat flux) Ith, and Ith is 55 W/m² in this example.

Figures 11A, 11B:
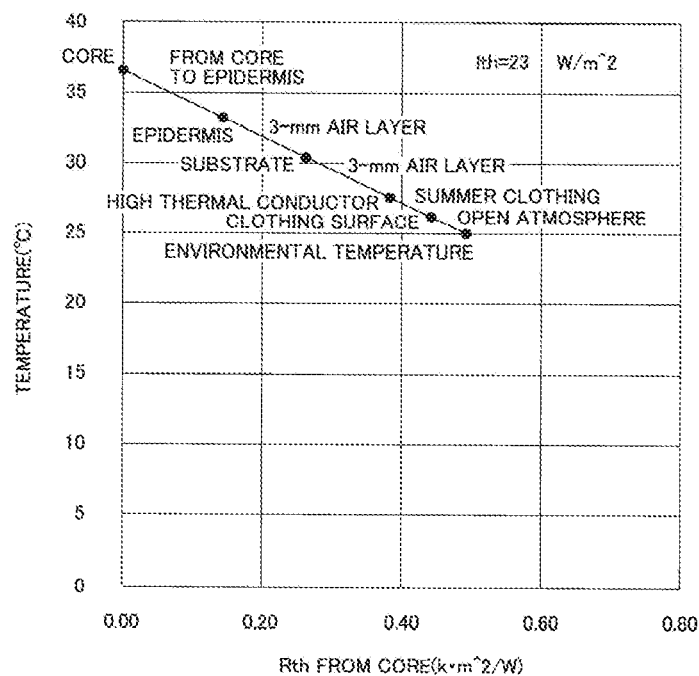
FIG. 11(a) shows a graph illustrating a temperature gradient from a body core to an environmental temperature in the summer.
FIG. 11(b) shows a table illustrating a thermal resistivity, a thickness and a thermal resistance of each case in the summer, in the first to fourth embodiments of the present invention.

A graph shown in FIG. 11(a) indicates a transition of the heat flow (heat flux) in each case in the summer, where a horizontal axis denotes the thermal resistance Rth (K·m²/W) and a vertical axis denotes the temperature (° C.). This graph is drawn assuming that it is the summer season where, for example, the deep body temperature is 36.5° C., the environmental temperature is 25° C., and the user wears shirts only.

See a table shown in FIG. 11(b) for data on thermal resistivity and thermal of each case, including: a region from the body core to the body surface (assuming that the depth is 25 mm), stationary atmosphere (assuming that 3-mm air layers are formed above and below the substrate, respectively), summer clothing (assuming that 1-mm air layer is formed under the shirts), and open atmosphere (with convention).

In the graph of FIG. 10(b), a gradient (T/Rth) of the straight line is the heat flow (heat flux) Ith, and Ith is 23 W/m² in this example.

A correlation between the thermal resistance and the temperature in each case for the biological data measurement device 1 with the two thermometers, according to the fifth embodiment of FIG. 5, when measuring the body temperature will be described with reference to FIG. 12.

Figures 12A, 12B:
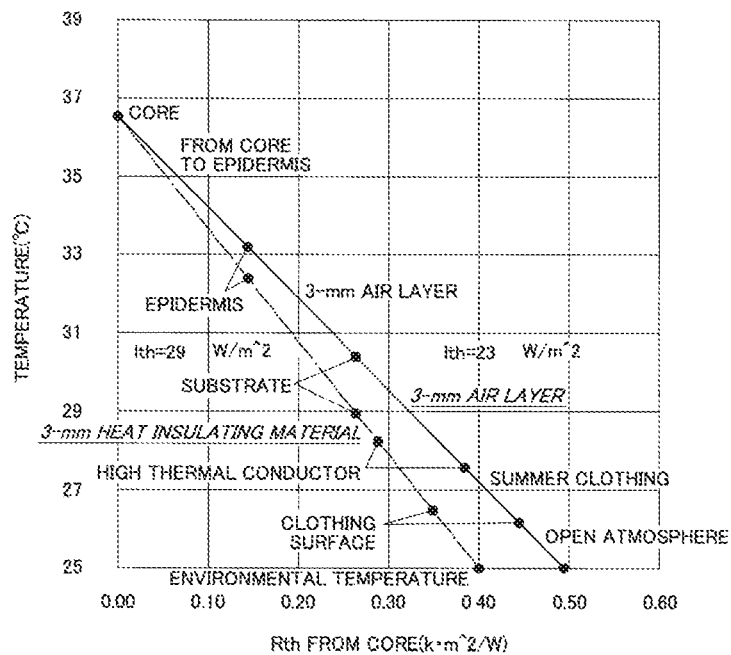
FIG. 12(a) shows a graph illustrating a temperature gradient from a body core to an environmental temperature, which is measured by a first thermometer and a second thermometer.
FIG. 12(b) shows a table illustrating a thermal resistivity, a thickness and a thermal resistance of each case at that time, in the fifth embodiment of the present invention.
Figure 13A:
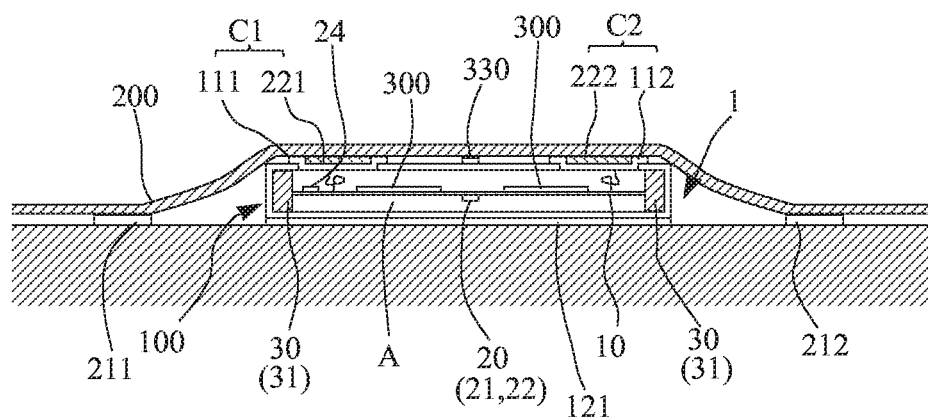
FIG. 13(a) shows a schematic cross-sectional view illustrating a biological data measurement device attached onto the body surface via a wearing belt.
Figure 13B:
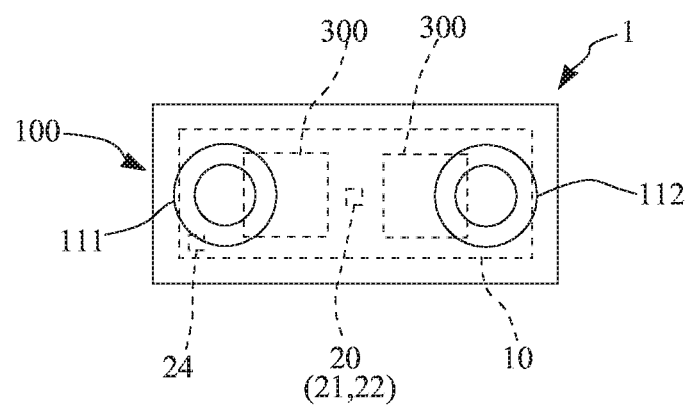
FIG. 13(b) shows a plan view of the biological data measurement device, in a ninth embodiment of the present invention.

A graph shown in FIG. 12(a) is drawn assuming that it is the summer season, where the deep body temperature is 36.5° C., the environmental temperature is 25° C., and the user wears shirts only, as in the graph of FIG. 11(a).

See a table shown in FIG. 11(b) for data on thermal resistivity and thermal of each case, including: a region from the body core to the body surface (assuming that the depth is 25 mm), stationary atmosphere (assuming that 3-mm air layers are formed above and below the substrate of the second thermometer 20b, respectively), heat insulating material (assuming that polystyrene having a thickness of 3 mm is provided on the upper surface of the substrate of the first thermometer 20a), summer clothing (assuming that 1-mm air layer is formed under the shirts), and open atmosphere (with convention).

In the graph of FIG. 12(a), a broken line denotes the heat flow Ith1 measured by the first thermometer 20a, and a solid line denotes the heat flow Ith2 measured by the second thermometer 20b. Since the heat flow Ith1 is different from the heat flow Ith2, the deep body temperature Tcore can be calculated based on the body surface temperature Tsk, the heat flow Ith1 and the heat flow Ith2.

As described above, the biological data measurement device of the present invention is configured to include the substrate, the infrared thermometer and the substrate thermometer, both of which are installed on the substrate, and the support member for supporting the substrate at a position spaced the predetermined distance from the body surface as a basic configuration. Thus, a simple configuration can be implemented with a low cost. Moreover, since the heat insulating layer between the substrate and the body surface is the air layer, the thermal resistance between the substrate and the body surface can be increased.

The biological data measurement device 1 according to a ninth embodiment will be described with reference to FIGS. 13(a), 13(b), 14(a) and 14(b). The biological data measurement device 1 is provided with a case 100 attached onto the body surface, such as chest, abdomen or the like, using a wearing belt 200.

The case 100 is made of a box body including a bottom plate, side plates and an upper lid. The substrate 10 is supported via the support member 30 made of the heat insulating material 31 in the case 100, thereby forming a predetermined space A between the bottom plate and the substrate 10. The thermometer 22, including the infrared thermometer 21 and the substrate thermometer 22, is disposed on a bottom surface side of the substrate 10, as in the embodiments stated above.

The case 100 basically adopts a configuration of the respective embodiments stated above, and an environmental thermometer 330 for measuring an ambient temperature is additionally disposed on an outer surface of the upper lid of the case 100 in the ninth embodiment. The environmental thermometer 330 does not need to have particular specification, and may employ commercially available products.

The substrate 100 is further provided with various signal processing circuit clusters 300. In the ninth embodiment, the signal processing circuit cluster 300 includes an ECG (electrocardiogram) measurement circuit 310, a GSR (galvanic skin resistance) measurement circuit 311 as in vivo electrical resistance measurement means for measuring an electrical resistance of the skin (in vivo), a GSR driving circuit 312, a communication circuit 313, a control circuit 314, a memory circuit 315, a power supply circuit 316 and a battery 317.

The communication circuit 313 includes the transmitter 24 and performs communication with the outside. The control circuit 314 employs a microcomputer, CPU, MPU, etc., and controls each circuit. The memory circuit 315 stores raw data, calculation results and the like. The power supply circuit 316 converts the voltage of the battery 317 to a predetermined voltage and supplies the power to each circuit.

The wearing belt 200 is provided with two electrodes 211, 212, both of which are in contact with the body surface. Contact portions C1, C2, both of which connect the electrodes 211, 212 to each circuit, i.e. the ECG measurement circuit 310, the GSR measurement circuit 311, and the GSR driving circuit 312, are provided between the wearing belt 200 and the case 100.

The contact portion C1 includes a combination of a male contact 221 connected to one electrode 211 via a wiring on a side of the wearing belt 200, and a female contact 111 provided on the upper lid of the case 100 as an engaging side of the male contact 221.

The contact portion C2 includes a combination of a male contact 222 connected to the other electrode 212 via a wiring on a side of the wearing belt 200, and a female contact 112 provided on the upper lid of the case 100 as an engaging side of the male contact 222.

In this example, the ECG measurement circuit 310, the GSR measurement circuit 311 and the GSR driving circuit 312 are connected to the female contacts 111, 112. The electrodes 211, 212 are simultaneously used in the ECG measurement and the GSR measurement.

It is preferable that a disk-shaped conductive magnet, similar to a coin or a button, is used in the male contacts 221, 222, and a dish-shaped magnetic element is used in the female contacts 111, 112. However, the conductive magnet may be used in the male contact, the magnetic element may be used in the female contact, or alternatively, both male and female contacts may use the conductive magnets.

It should be noted that the terms "male" and "female" for the contacts are for easier understanding. It is unnecessary that the male contact has to be a projection and the female contact has to be a recess. The male contact can be referred as to a first contact, and the female contact as to a second contact.

Figure 14A:
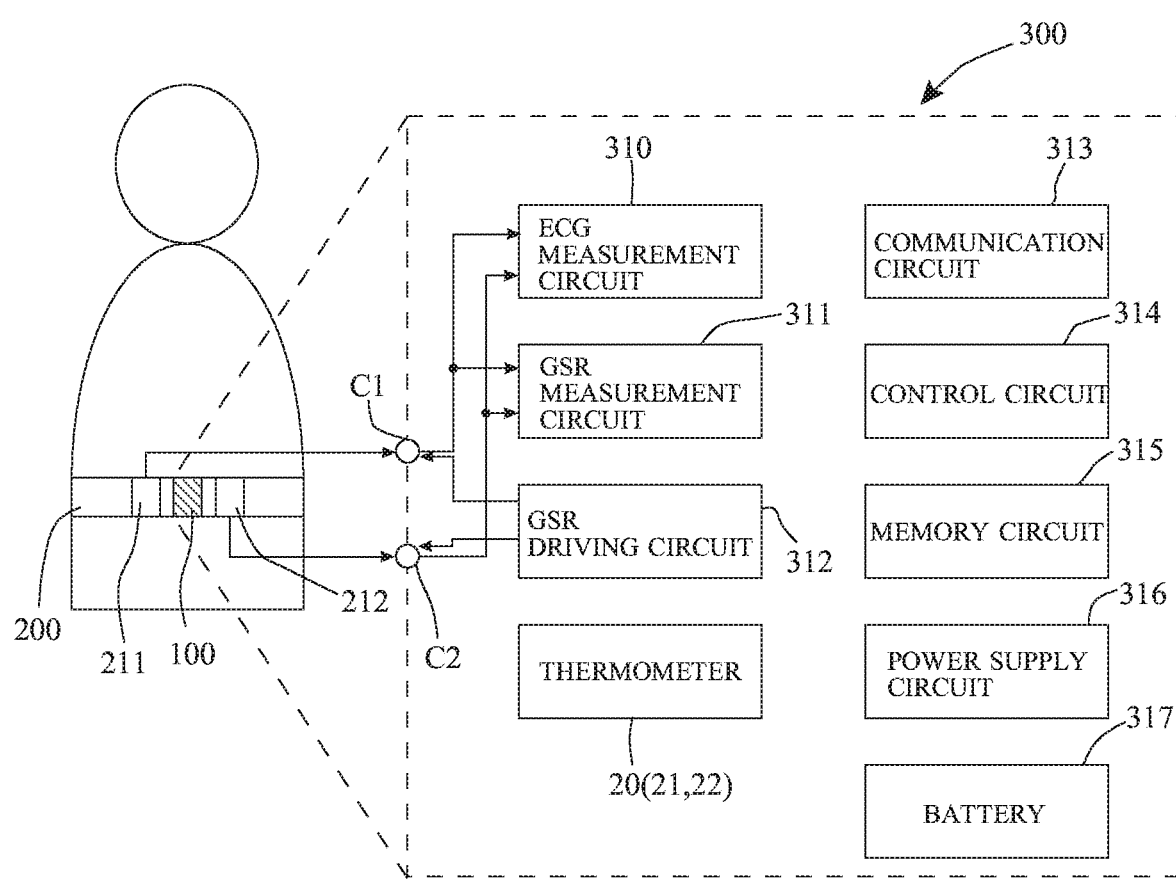
FIG. 14(a) is a schematic view illustrating a circuit system installed on a substrate of the biological data measurement device according to the ninth embodiment, and an exemplified arrangement of electrodes (two) provided on the wearing belt.
Figure 14B:
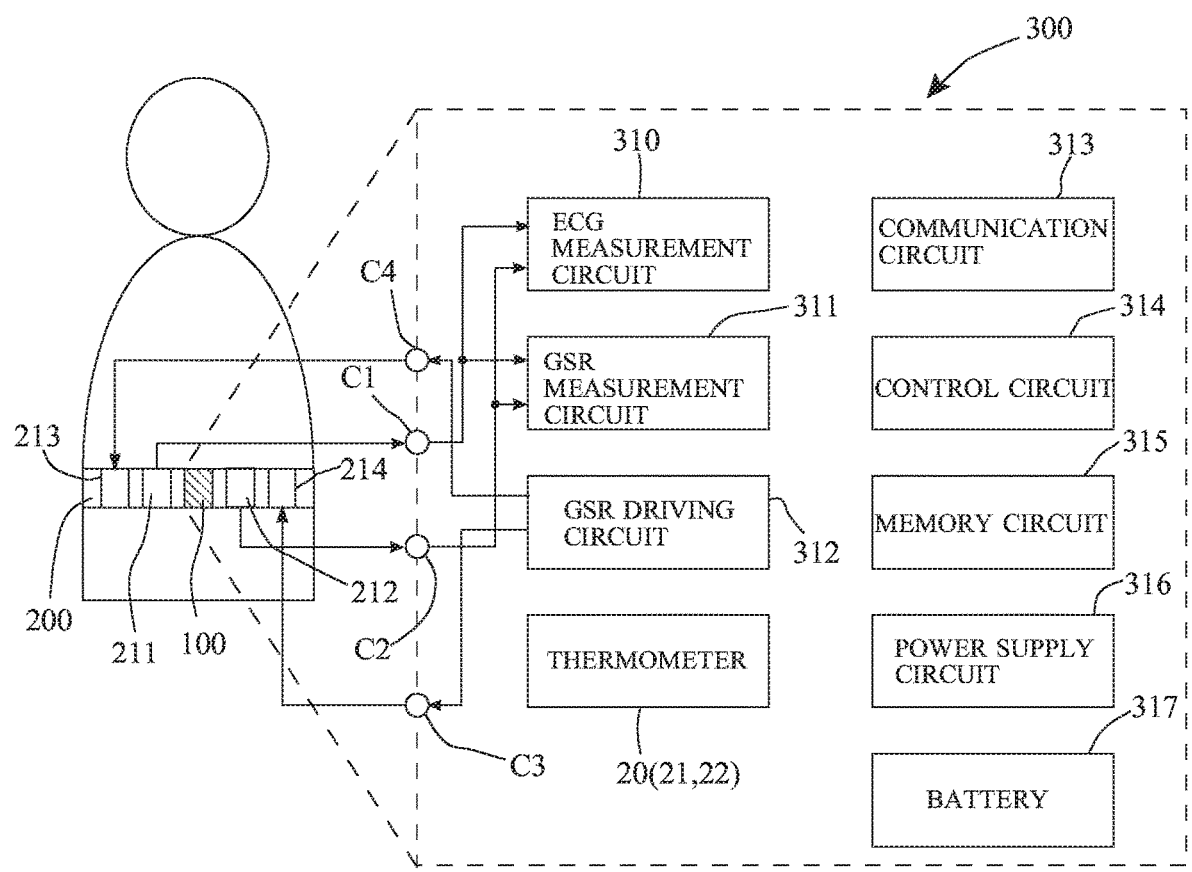
FIG. 14(b) is a schematic view illustrating another exemplified arrangement of electrodes (four) provided on the wearing belt, in the ninth embodiment.

As a modified example, two electrodes 213, 214 may be added outwardly of the electrodes 211, 212, as four electrodes in total, accompanying with additional contact portions C3, C4, as shown in FIG. 14(b). The contact portions C3, C4 may have the same configuration as the contact portions C1, C2.

In this case, the GSR driving circuit 312 is connected to the additional outer electrodes 213, 214 via the contact portions C3, C4, thereby supplying a drive current from the GSR driving circuit 312 to the electrodes 213, 214.

The ECG measurement circuit 310 and the GSR measurement circuit 311 are connected to the inner electrodes 211, 212 via the contact portions C1, C2, thereby measuring a GSR voltage while simultaneously measuring an ECG signal with the electrodes 211, 212.

As described above, it is possible to eliminate influence of contact resistance between the electrode and the skin by dividing the four electrodes 211 to 214 into the electrodes 213, 214 on a drive current supplying side and the electrodes 211, 212, on a voltage measurement side, as a four-electrode (four-terminal) method. This mechanism is particularly effective when a GSR absolute value is important. Another advantageous effect is that an electrocardiogram (ECG) voltage measurement is hardly influenced by a noise caused by GSR driving.

As described above, in the ninth embodiment, the ECG measurement circuit 310 is provided for measuring the electrocardiogram. Therefore, a physiological state of the user can be confirmed with higher accuracy by simultaneously measuring the electrocardiogram (ECG) with the deep body temperature Tcore obtained by a temperature measurement system including the thermometer 20.

That is, the deep body temperature Tcore responds late to exercise load and/or environmental fluctuation. Meanwhile, heart rate obtained from the ECG responds immediately (sensitively) to the exercise load. Therefore, exercise status of the user, including start, continuation or termination of the exercise, can be confirmed by adopting the ECG measurement together with the deep body temperature measurement.

It is possible to send a warning to the user him/herself or a supervisor of the user to cease the exercise when the deep body temperature Tcore exceeds a predetermined threshold value. The environmental fluctuation can be grasped the substrate temperature Tsub and other thermometers, and thus it is possible to issue environment alerts in the same way. As described above, since the environmental thermometer 330 is disposed on the outer surface of the upper lid of the case 100, the measured temperature value of the environmental thermometer 330 can also be reflected to the deep body temperature Tcore.

It is preferable that an adhesive film 121 made of silicone or the like is provided on the bottom surface of the case so that no gap is formed between the skin and the bottom plate of the case, and further the case 100 is not shifted due to sweating, when the case 100 is attached onto the body surface by the wearing belt 200.

A time constant correction of a tenth embodiment will be described with reference to FIGS. 15(a) and 15(b). The body surface temperature Tsk often temporally lags behind the substrate temperature Tsub due to the subcutaneous thermal resistance and heat capacity. This is because the substrate temperature Tsub depends on the ambient temperature and the heat capacity of the substrate 10 is relatively small.

Figure 15A:
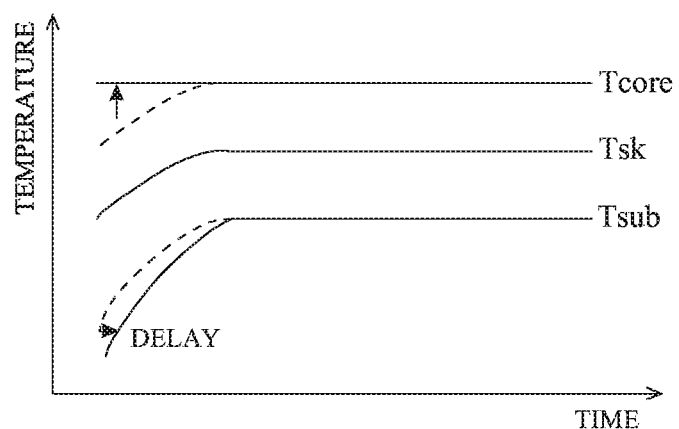
FIG. 15(a) shows graph illustrating time constant correction of the detected body surface temperature and the substrate temperature.
Figure 15B:
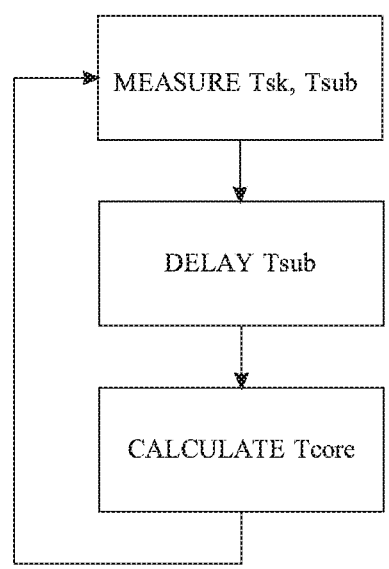
FIG. 15(b) shows a flowchart illustrating a step of executing the time constant correction, in a tenth embodiment of the present invention.

Calculation failures occur in the deep body temperature Tcore due to the temporal delay of the body surface temperature Tsk, as indicated by a broken line of FIG. 15(a). The calculation errors of the deep body temperature Tcore can be reduced by adding a predetermined delay to the substrate temperature Tsub and eliminating a delay difference with the body surface temperature Tsk.

A delay amount Tsub_d for the substrate temperature Tsub is created by calculating the equation, for example, $Tsub\_d[n+1]=Tsub\_d[n]+(Tsub[n+1]-Tsub\_d[n])/\tau sub$, using time series data such as Tsub[n−1], Tsub[n], Tsub[n+1] . . . , thereby obtaining the delay amount Tsub_d for the substrate temperature Tsub.

As one example, a time constant of about 50 seconds can be added to the substrate temperature Tsub as a delay amount by setting τsub to about 50 if the time series data exists every second.

Since there is a correlation between the in vivo thermal resistance Rthbody and τsub, it is possible to select τsub in response to a value of the in vivo thermal resistance Rthbody based on a correlation table prepared in advance. Sometimes overshoot (refer to a broken line in FIG. 15(a)) may appear when, for example, the user starts to wear the biological data measurement device 1 onto the body surface. It is also possible to store a shape of the overshoot and remove it.

A method for obtaining the in vivo thermal resistance Rthbody from a transient response upon wearing will be described with reference to FIGS. 16(a) to 16(d), as an eleventh embodiment. According to this method, an absolute value of the deep body temperature can be obtained using the SHF (single-heat-flux) method.

Figure 16A:
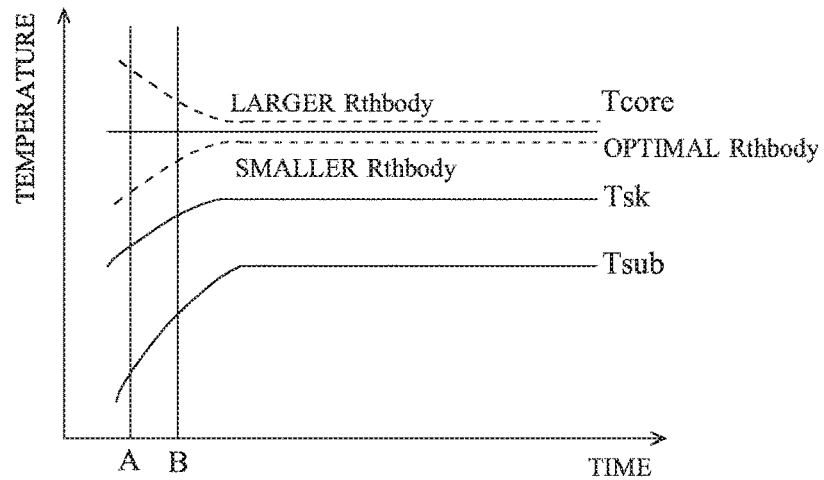
FIG. 16(a) is a graph illustrating a method for obtaining an in vivo thermal resistance Rthbody from a transient response at the time of wearing as an eleventh embodiment of the present invention.

After the user starts to wear the biological data measurement device 1, the heat flow Ith shifts from a large value to a small value. Referring to FIG. 16(a), the in vivo thermal resistance Rthbody, which is an unknown value, is obtained from two heat flows Ith at the timings A, B during the heat flows Ith shifts.

First, data is recorded before wearing in order to record the transient response at the time of wearing. An initial value of the in vivo thermal resistance Rthbody is set to a temporary value, but the overshoot appears by setting the in vivo thermal resistance Rthbody to a relatively large value. A timing A is set as a first timing around at the time when the overshoot appears. Consequently, it is possible to avoid an unstable period in an initial stage of wearing.

A timing B, as a second timing, is preferably set to a timing about several minutes, preferably about 5 to 10 minutes, after the timing A. If the elapsed time is shorter than about 5 to 10 minutes, the faults easily occur since there is not enough time to change from the timing A. If the elapsed time is longer than about 5 to 10 minutes, the body temperature of the user may change, which is not preferable.

Figure 16B:
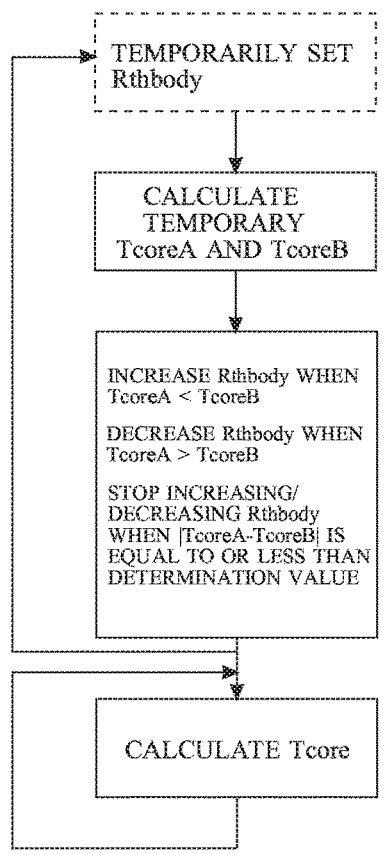
FIG. 16(b) is a flowchart illustrating steps of increasing and decreasing the in vivo thermal resistance Rthbody by the method.

Referring also to the flowchart of FIG. 16(b), a deep body temperature TcoreA at the timing A and a deep body temperature TcoreB at the timing B are calculated based on the temporarily set value of the in vivo thermal resistance Rthbody, and then TcoreA is compared with TcoreB.

Accordingly, in a case where TcoreA is smaller than TcoreB, a value of the in vivo thermal resistance Rthbody is increased; on the other hand, in a case where TcoreA is larger than TcoreB, a value of the in vivo thermal resistance Rthbody is decreased, thereby calculating the deep body temperature Tcore again.

In a case where an absolute value of TcoreA−TcoreB, |TcoreA−TcoreB|, is equal to or falls below a determination value, a value at that time is adopted as a value of the in vivo thermal resistance Rthbody, increase/decrease in Rthbody is ceased and the deep body temperature Tcore is finally calculated.

Regarding increase/decrease the in vivo thermal resistance Rthbody, it is possible to use a binary search that sequentially halves a change amount of increase/decrease. In a case where a solution cannot be found, it is possible to instruct the user to wear the device again; or alternatively, it is also possible to use the previously obtained value. The accuracy can be further improved by storing the in vivo thermal resistance Rthbody for each region, such as abdomen, back, etc., and by averaging for each region.

It is also possible to determine a gradient of the deep body temperature Tcore from several points between sections A and B using a differential waveform of the deep body temperature Tcore between the sections A and B after the overshoot is eliminated, instead of comparison between TcoreA and TcoreB.

Figure 16C:
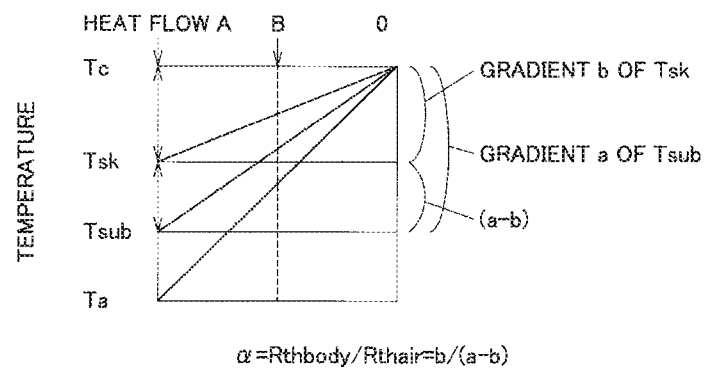
FIG. 16(c) is a graph illustrating a method for directly obtaining the in vivo thermal resistance based on the body surface temperature and the substrate temperature as another method of the eleventh embodiment.
Figure 16D:
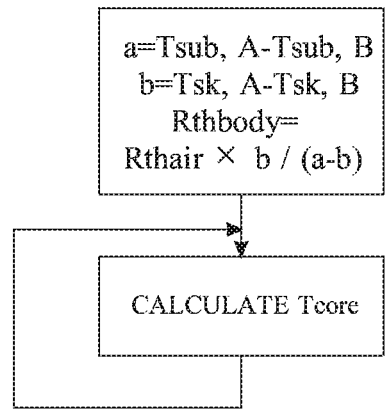
FIG. 16(d) is a flowchart illustrating operations according to another method of the eleventh embodiment.

Referring to FIGS. 16(c) and 16(d), it is also possible to, further mathematically, determine the in vivo thermal resistance Rthbody directly from gradients of the substrate temperature Tsub and the body surface temperature Tsk.

That is, a gradient of the substrate temperature Tsub obtained from a difference between the substrate temperature TsubA at the timing A and the substrate temperature TsubB at the timing B is a, and a gradient of the body surface temperature Tsk obtained from a difference between the body surface temperature TskA at the timing A and the body surface temperature TskB at the timing B is b. Then, it is only necessary to find a state where a gradient of the deep body temperature Tcore is zero. As it is apparent from definitions of the in vivo thermal resistance Rthbody and the thermal resistance Rthair of the air layer, the gradient of the deep body temperature Tcore is zero when Rthbody/Rthair is b/(a−b).

The thermal resistance Rthair of the air layer A is already known, and the gradients a, b of the substrate temperature Tsub and the body surface temperature Tsk are obtained from respective temperatures at the timings A, B as described above. Therefore, the in vivo thermal resistance Rthbody can be directly obtained from the equation Rthair× b/(a−b).

The gradients a, b of the substrate temperature Tsub and the body surface temperature Tsk can be respectively obtained by differentiating, and thus it is also possible to directly obtain a value of Rthbody/Rthair using differential values corresponding to the gradients. Since the thermal resistance Rthair of the air layer can be recognized by calibration, the in vivo thermal resistance Rthbody, which is unknown, is obtained.

A method for obtaining a value of Rthbody so that the absolute value of TcoreA−TcoreB falls within a predetermined determination value, as described above, includes a method for directly obtaining Rthbody without such repetitive calculation.

According to the DHF method, the deep body temperature Tcore is obtained using two heat flows measured at spatially distant places. Whereas the invention according to the eleventh embodiment adopts the SHF method, while the absolute value of the deep body temperature Tcore can be obtained from the heat flows measured in the same place but at the timings A, B, which are temporally away from each other.

As described above, two heat flows are measured in the same place at the timing A and the timing B, which are temporally away from each other, using the same thermometer. Consequently, it is hardly influenced by variation due to place or thermometer. Furthermore, the biological data measurement device can be downsized with the significantly reduced power consumption, as compared with those employing the DHF or ZHF method.

However, this method can be established provided that the deep body temperature Tcore has not changed, while the heat flow at the timing A is needed to be different from the heat flow at the timing B. Furthermore, it is necessary to execute processes when the environmental temperature changes at a rate at which the deep body temperature Tcore cannot change yet.

The measuring object in the invention according to the eleventh embodiment is not limited to the living organism, but the invention may be applied to a structure having a heat source at depths, for example, electronic or electric devices, air conditioners, cooking devices, machine facilities, transport devices, buildings, geological researches and the like. In addition, when the device is attached to the living organism, It can be mounted on a part of clothing, shoes, hat, gloves, earpieces, eyeglasses, etc.

Therefore, in the present invention, an object having a first thermal resistance from a core to a surface is a measuring object. The present invention also encompasses a biological data measurement device which is provided with a heat insulating layer which is disposed on a surface of the measuring object and has a second thermal resistance; measurement means for measuring a first and a second temperatures, which is segregated by the heat insulating layer; calculation means for calculating the first thermal resistance based on the first and the second temperatures measured at a first timing A, and the first and the second temperatures measured at a second timing B after a predetermined time has elapsed from the first timing A; and calculation means for calculating a deep body temperature of the measuring object based on the first and the second thermal resistances, and the first and the second temperatures.

In a case where the measuring object is the living organism, the first thermal resistance corresponds to the in vivo thermal resistance Rthbody, the heat insulating layer having the second thermal resistance corresponds to the air layer having the air thermal resistance Rthair, and the first and second temperatures respectively correspond to the body surface temperature Tsk and the substrate temperature Tsub.

A method for obtaining the in vivo thermal resistance Rthbody using a heating element, such as a heater, will be described with reference to FIGS. 17(a) and 17(b) as a twelfth embodiment.

In this embodiment, a ZHF (zero-heat-flux) state is temporarily created by raising a case temperature to the deep body temperature Tcore, thereby calculating the in vivo thermal resistance Rthbody based on the ZHF state.

When the substrate temperature Tsub and the body surface temperature Tsk coincide with the deep body temperature Tcore, the heat flow Ith does not flow (ZHF state). The ZHF state can be confirmed when substrate temperature Tsub and the body surface temperature Tsk become the same temperature. The in vivo thermal resistance Rthbody is calculated back so that the coincident temperature is an answer for the calculation of the deep body calculation Tcore immediately before or after Tsub and Tsk coincide with Tcore.

In particular, the case temperature Tcase rises by placing a heating element, such as a heater or a hot pack, on the case 100 (refer to FIG. 13). Hands or arms may be placed on the case 100 as the heating element. It is preferable to notify the user beforehand so that calibration using the heating element shall be done at rest since the measurement failures occur if the true deep body temperature of the user fluctuates during the calibration.

It is preferable that, for example, a accept button for the calibration using the heating element is provided at any position of the case 100 to receive the instruction from the user. A concept of the calibration reception encompasses that a system automatically drives the heating element provided in the case 100 to carry out the calibration without the instruction from the user. The user may be instructed to place the heating element on the case if needed.

Figure 17A:
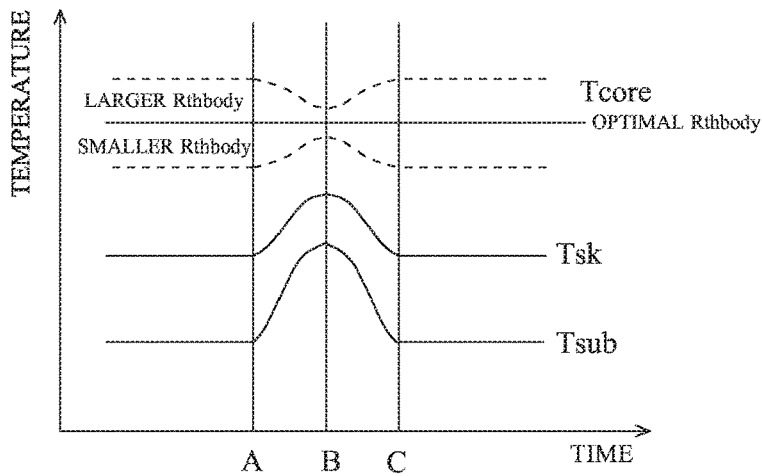
FIG. 17(a) shows a graph illustrating a method for obtaining an in vivo thermal resistance Rthbody using a heating element.
Figure 17B:
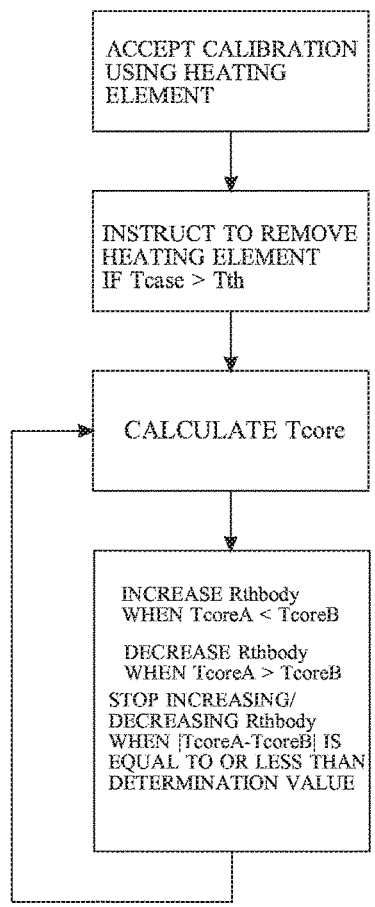
FIG. 17(b) shows a flowchart illustrating steps of increasing and decreasing the in vivo thermal resistance Rthbody by the method, as a twelfth embodiment of the present invention.

The case temperature Tcase increases by the heating element (from timing A to timing B, in FIG. 17(a)). When the case temperature Tcase exceeds a predetermined temperature Tth by the heating, the user is instructed to remove the heating element from the case 100. Or alternatively, the heating may be automatically ceased. Instead of the case temperature Tcase, for example, the substrate temperature Tsub or the body surface temperature Tsk may be employed.

As in the eleventh embodiment, calculation and determination of the deep body temperatures TcoreA, TcoreB at the timings A, B are repeated to obtain the optimal in vivo thermal resistance Rthbody. It is also possible to use data on the timings B, C both at which the temperature decreases.

Furthermore, upward or downward projection shapes of the deep body temperature Tcore may be determined using all measurement points from the timing A to the timing C in various ways (for example, using the differential waveform of Tcore, etc.). As another aspect, a cooling element may be used instead of the heating element.

A method for obtaining the in vivo thermal resistance Rthbody from fluctuation in the environmental temperature will be described with reference to FIGS. 18(a) and 18(b) as a thirteenth embodiment.

The inventors have confirmed from experiments that quite lots of discontinuous points appear in the calculated value of the deep body temperature Tcore when a value of the in vivo thermal resistance Rthbody is deviated, upon normally using. This is because, as long as the in vivo thermal resistance Rthbody is deviated, the calculated value of the deep body temperature Tcore fluctuates even when the true deep body temperature Tcore is constant (in the experiment, the rectal temperature is simultaneously observed for verification).

This fluctuation is caused by the deviation in the in vivo thermal resistance Rthbody and the changes in the environmental temperature. In actual practice, it is unclear whether or not the true body temperature Tcore is constant. However, in a period during when the deep body temperature Tcore is unlikely to be changed so much, for example, in a case where a rapid change in the environmental temperature (a change within several minutes), as fast as the deep body temperature Tcore does not significantly change, is detected, the in vivo thermal resistance Rthbody is calculated at the timings A, B as described above.

When the user is exercising, a sudden change in the body temperature may occur. Thus it is preferable to execute a step of obtaining the in vivo thermal resistance Rthbody when a heart rate is equal to or less than a threshold value, as shown in FIG. 18(b).

Figure 18A:
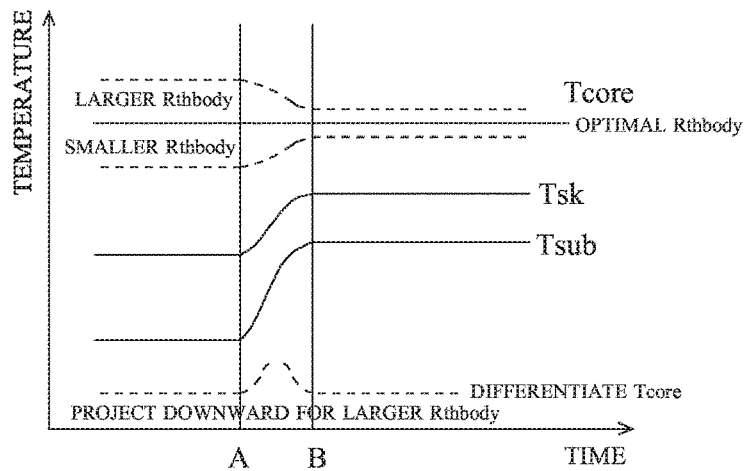
FIG. 18(a) shows a graph illustrating a method for obtaining an in vivo thermal resistance Rthbody using a heating element.
Figure 18B:
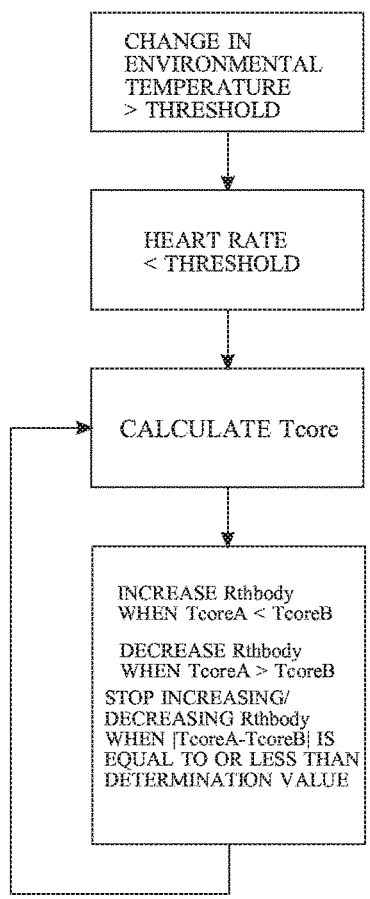
FIG. 18(b) shows a flowchart illustrating steps of increasing and decreasing the in vivo thermal resistance Rthbody by the method, as a thirteenth embodiment of the present invention.

When the in vivo thermal resistance Rthbody is calculated at the timings A, B, differential waveforms of the deep body temperatures Tcore at the timings A, B may be observed to carry out the calculation, as indicated by a dotted line of FIG. 18(a).

Even in a case where the true deep body temperature Tcore gradually changes, the gentle change can be offset by using the differential waveform, so that the change from the offset can be easily determined. For the differential waveform, a high-order differentiation, i.e. at least the second order differentiation may be used.

For example, the in vivo thermal resistance Rthbody is calculated at a timing when the environmental temperature significantly changes during the user wears the biological data measurement device for a day, and the in vivo thermal resistance Rthbody is more accurately determined by calculating in accordance to the reliability from several values of the in vivo thermal resistance Rthbody.

Figure 19A:
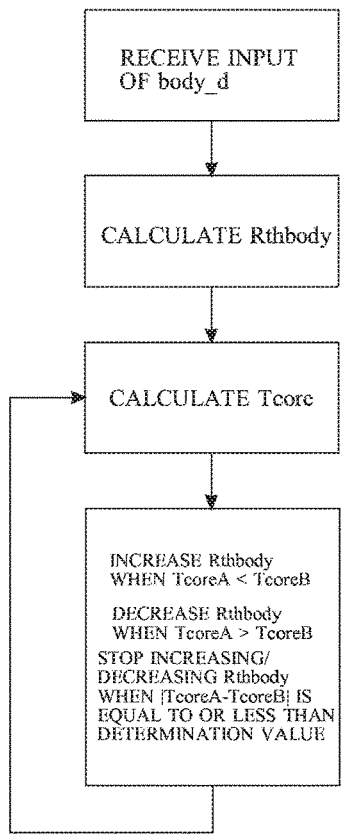
FIG. 19(a) is a flowchart illustrating a method for requesting to a user to input a distance (body_d) from a body core to epidermis, as a fourteenth embodiment of the present invention.

A method for requesting to the user to input a distance body_d from a body core to epidermis will be described with reference to FIG. 19(a) as a fourteenth embodiment.

According to the fourteenth embodiment, the user is requested to input an in vivo body core distance body_d, which is a distance from the body core to the epidermis (body surface), as an alternative when a proper value of the in vivo thermal resistance Rthbody cannot be obtained in the eleventh embodiment stated above (the method for obtaining the in vivo thermal resistance Rthbody from the transient response upon wearing).

The in vivo thermal resistance Rthbody can be obtained by multiplying the in vivo body core distance body_d by the thermal resistivity from the body core to the epidermis. As a method for the user to know the in vivo body core distance body_d, it is possible to obtain a temporary in vivo thermal resistance Rthbody based on a measured region and statistical data by inputting height and weight, in addition to a method using the GSR. As described above, the in vivo thermal resistance Rthbody can be updated to a more accurate value during the measurement as appropriate.

As another method, the body temperature at rest is input and received, and the in vivo thermal resistance Rthbody is calculated back from the substrate temperature Tsub and the body surface temperature Tsk, both of which are obtained at an initial stage of the measurement, so that the deep body temperature Tcore coincides with the received temperature, instead of requesting the user to input the in vivo body core distance body_d.

The rectal temperature at rest is 37° C.±0.2° C., of which individual difference is small. Since the abdominal temperature falls within a range of about ±0.5° C. with respect to the rectal temperature, a value around 37° C. can be used as an initial value when the temperature at rest cannot be input.

Figure 19B:
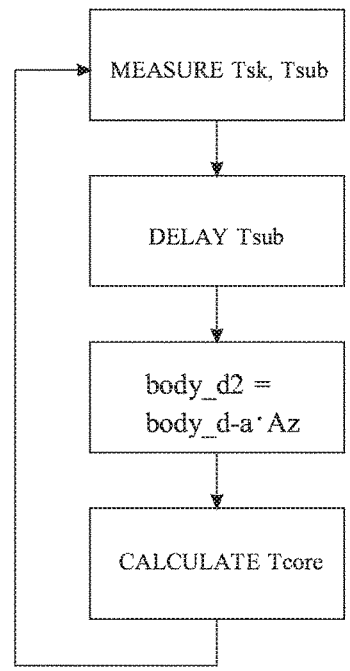
FIG. 19(b) is a flowchart illustrating a method for detecting a posture from acceleration to correct a body surface temperature and a substrate temperature, as a fifteenth embodiment of the present invention.

A posture correction based on acceleration will be described with respect to FIG. 19B as a fifteenth embodiment. In this case, the biological data measurement device 1 is provided with an accelerometer (acceleration sensor), as will be described later.

Since the in vivo body core distance body_d may change depending on the user's posture (for example, standing posture and lying posture), the influence of the posture can be reduced using a value of acceleration obtained by the accelerometer.

When Az is acceleration in a direction perpendicular to the body surface of the user (Az is 0 when the user is sitting or standing, and Az is 1G when the user is in a supine position [G is a gravitational acceleration]), the corrected in vivo body core distance body_d2 from the body core to the body surface is obtained from the equation body_d−a×Az, in which a is a coefficient and acquired from experiments or the like.

The in vivo thermal resistance Rthbody is calculated using the corrected in vivo body core distance body_d2 to acquire the deep body temperature Tcore. Furthermore, the convection of the air layer A in the case 100 varies depending on a direction with respect to the gravitational acceleration to fluctuate a heat conductivity of the air layer A, which may cause a problem. Also in this case, the present invention encompasses that the thickness and the thermal resistance of the air layer A are corrected using the acceleration such as Az.

Additionally, the air layer A in the case 100 slightly changes depending on the environmental conditions such as atmospheric pressure, humidity, etc. Therefore, it is possible to correct the air layer using the atmospheric pressure or the humidity, measured at the same time, in response to a target accuracy of the body temperature measurement.

The biological data measurement device 1 can be calibrated using a hot plate, a constant temperature bath, or the like. The infrared thermometer 21 is placed on the hot plate assuming that the hot plate is the skin, and the environmental temperature is varied in the constant temperature bath. The thermal resistance of the air layer is obtained from the calibration.

The algorithm used in the present invention can be executed by the control circuit 314 installed in the biological data measurement device 1, or can be executed at a server on the cloud.

Figure 20A:
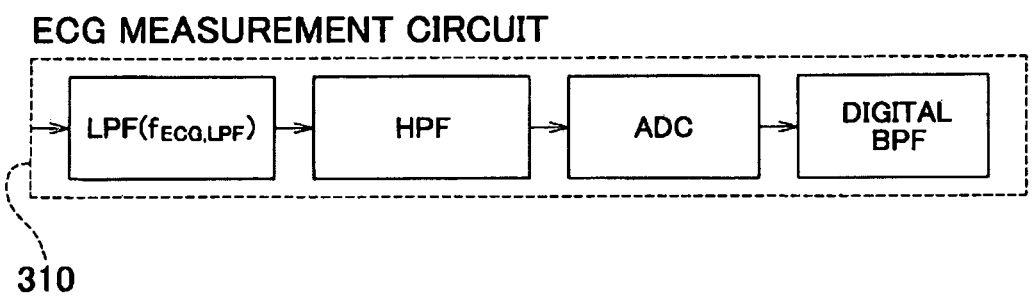
FIG. 20(a) shows a block diagram illustrating an ECG measurement circuit installed in the ninth embodiment.
Figure 20B:
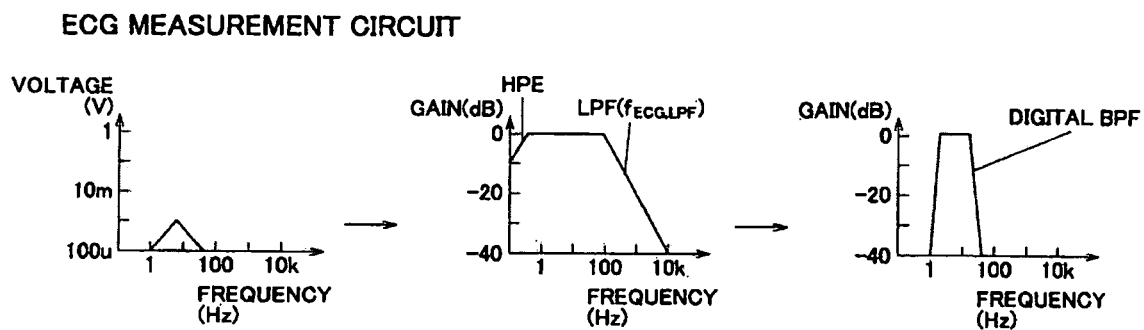
FIG. 20(b) shows an explanatory view illustrating operations of each part thereof, as a sixteenth embodiment of the present invention.
Figure 21A:
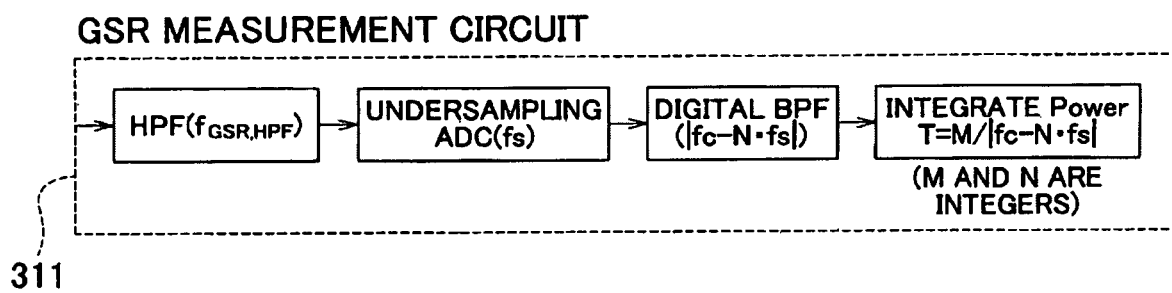
FIG. 21(a) shows a block diagram illustrating a GSR measurement circuit installed in the ninth embodiment.
Figure 21B:
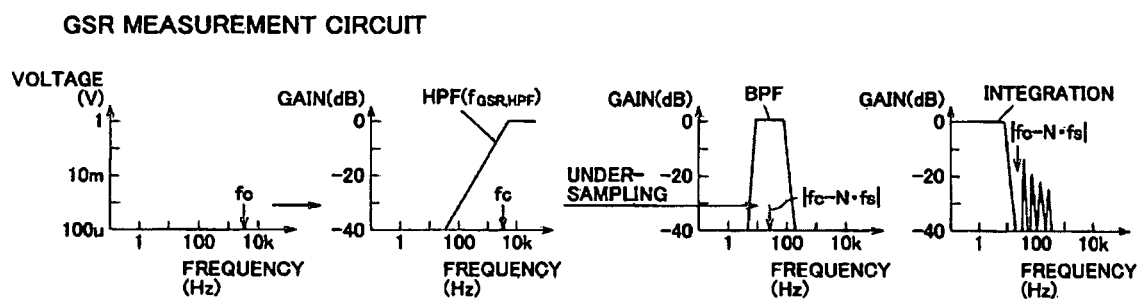
FIG. 21(b) shows an explanatory view illustrating operations of each part thereof, as a sixteenth embodiment of the present invention.
Figure 22A:
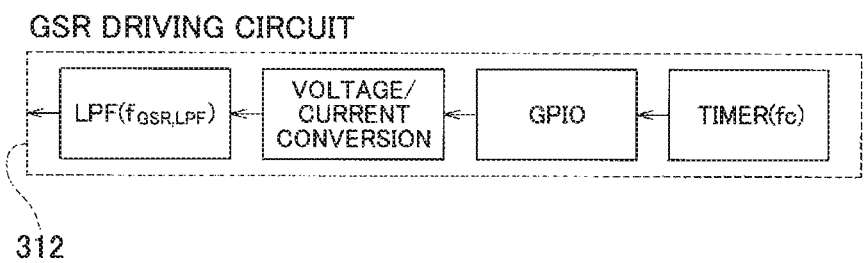
FIG. 22(a) shows a block diagram illustrating a GSR driving circuit installed in the ninth embodiment.
Figure 22B:
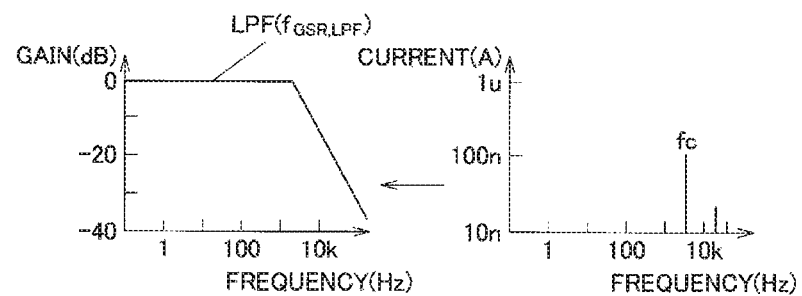
FIG. 22(b) shows an explanatory view illustrating operations of each part thereof, as a sixteenth embodiment of the present invention.

The ECG measurement circuit 310, the GSR measurement circuit 311, and the GSR driving circuit 312, which are installed in the biological data measurement device 1, will be described with reference to FIGS. 20 to 22, as a sixteenth embodiment.

Each of the ECG measurement circuit 310 and the GSR driving circuit 312 includes a low-pass filter (LPF), and the GSR measurement circuit 311 includes a high-pass filter (HPF). The cutoff frequencies are set to $f_{ECG, LPF} < f_{GSF, HPF} \cong f_{GSR, LPF}$.

The GSR measurement circuit 311 further includes an A/D converter for performing undersampling of fs, a band-pass filter (BPF) for passing |fc−N·fs| (N is an integer), and an integrator of T=1/|fc−N·fs|.

The biological data measurement device 1 is attached onto the skin (body surface) and measures the deep body temperature Tcore and the like for a long time. Thus, the heat generation needs to be extremely suppressed, and different approaches are required to reduce the power consumption. The basic frameworks realizing lower consumption using passive elements, lowering a sampling frequency to the limit, and signal processing with lower calculation amount.

An ECG signal frequency in the ECG measurement circuit 310 is several Hz to several tens Hz, and is set to, for example, several tens Hz to several hundred Hz as $f_{ECG, LPF}$, so that this signal frequency passes. The LPF removes a GSR driving signal set on a high frequency side. Since the ECG signal has a relatively wide band at 100 Hz or less, the A/D converter (ADC) executes Nyquist sampling while setting the sampling frequency to several tens Hz to several hundred Hz.

The GSR driving frequency fc in the GSR driving circuit 312 is set to several hundred Hz to several tens kHz avoiding the ECG signal frequency. It is set to, for example, several hundred Hz to several tens kHz as $f_{GSR, HPF}$ to remove 1/f noise and thermal noise.

In the GSR sampling, the A/D converter (ADC) performs the undersampling operation and sets as a sampling frequency fs to, for example, around 1 kHz. Although the sampling frequency is relatively high, intermittent operation is performed in a specific time window to reduce the power consumption. A time window avoiding a periphery of the R wave, which is a main peak timing of the ECG, is set as the specific time window, whereby it hardly influence the R wave measurement with time intervals.

The GSR signal appears at a frequency of |fc−N·fs| (N is an integer) by undersampling. For example, when fs is set to 1024 Hz and fc is set to 5028 Hz, the GSR signal appears at 32 Hz. 1/f noise, thermal noise and quantization noise are eliminated by narrowing a bandwidth to pass 32 Hz as a digital BPF.

Furthermore, by integrating the power of the signal (the square of the signal) with respect to the time of M/32 sec, a first null point appears at 32 Hz when, for example, M is 1. A carrier frequency of the GSR driving is set to match with a frequency of the null point, and thus it is possible to remove a carrier component with an extremely low calculation amount and to extract amplitude information which corresponds to the changes in the skin resistance.

The GSR phase information may be necessary in some cases when obtaining the in vivo body core distance body_d from the body core to the epidermis (body surface). The GSR driving signal passes subcutaneous fat and causes a certain phase shift. A thickness of the subcutaneous fat can be estimated by observing an amplitude at where the phase is shifted. The integration starts from the certain phase of the GSR driving signal in order to observe an amplitude at a specific phase of the GSR driving signal, thus it is possible to easily extract the amplitude of the specific phase.

The GSR driving frequency fc is set to several hundred Hz to several tens kHz. Additionally, the cutoff frequency $f_{GSR, LPF}$ of the LPF of the GSR driving circuit 312 are set to several hundred Hz to several tens kHz so that the GSR driving frequency fc passes and a high frequency is attenuated.

A seventeenth embodiment of the present invention will be described with reference to FIGS. 23 and 24. In the ninth embodiment as previously stated, when the biological data measurement device 1 is attached to the living organism, the case 100 is pressed against the body surface by the wearing belt 200. Meanwhile, in the seventeenth embodiment, the case 100 is placed on the wearing belt 200 and attached to the living organism.

The seventeenth embodiment employs a four-electrode method. As shown in FIG. 24, four electrodes 211, 212, 213, 214 are provided on a surface (rear surface) of the wearing belt 200, which is in contact with the body surface. Portions other than the electrodes 211, 212, 213, 214 are covered with an electrical insulating sheet 230 on the rear surface of the wearing belt 200.

Referring to FIG. 14(b), two inner electrodes 211, 212 are connected to the ECG measurement circuit 310 and the GSR measurement circuit 311 via the contact portions C1, C2, while two outer electrodes 213, 214 are connected to the GSR driving circuit 312 via the contact portions C3, C4.

The male contacts 221, 222, 223, 224, which respectively constitute the contact portions C1, C2, C3, C4, are provided on a surface (a back side of the paper in FIG. 24) of the wearing belt 200.

The electrode 211 is connected to the male contact 221 via a lead wiring 211a. The electrode 212 is connected to the male contact 222 via a lead wiring 212a. The electrode 213 is connected to the male contact 223 via a lead wiring 213a. The electrode 214 is connected to the male contact 224 via a lead wiring 214a.

Figure 23A:
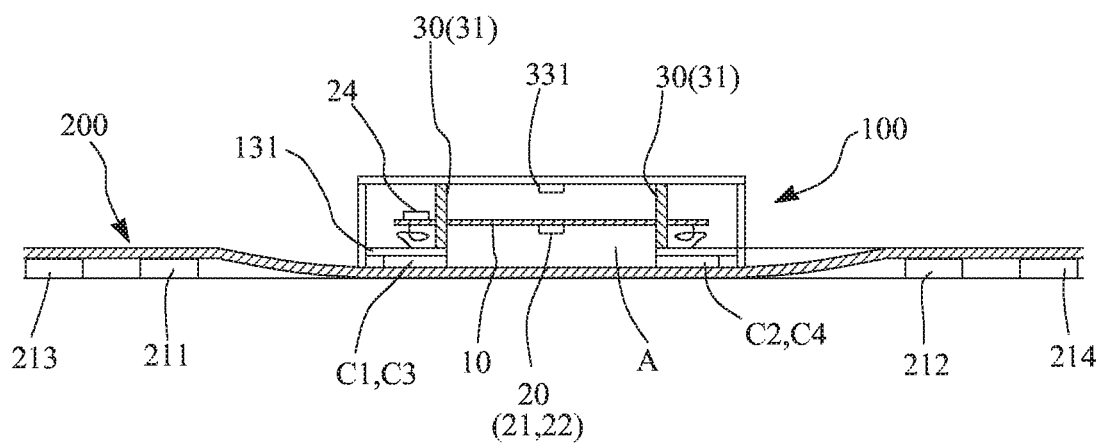
FIG. 23(a) shows a schematic cross-sectional view illustrating an aspect in which a case of a biological data measurement device is disposed on a wearing belt.
Figure 24:
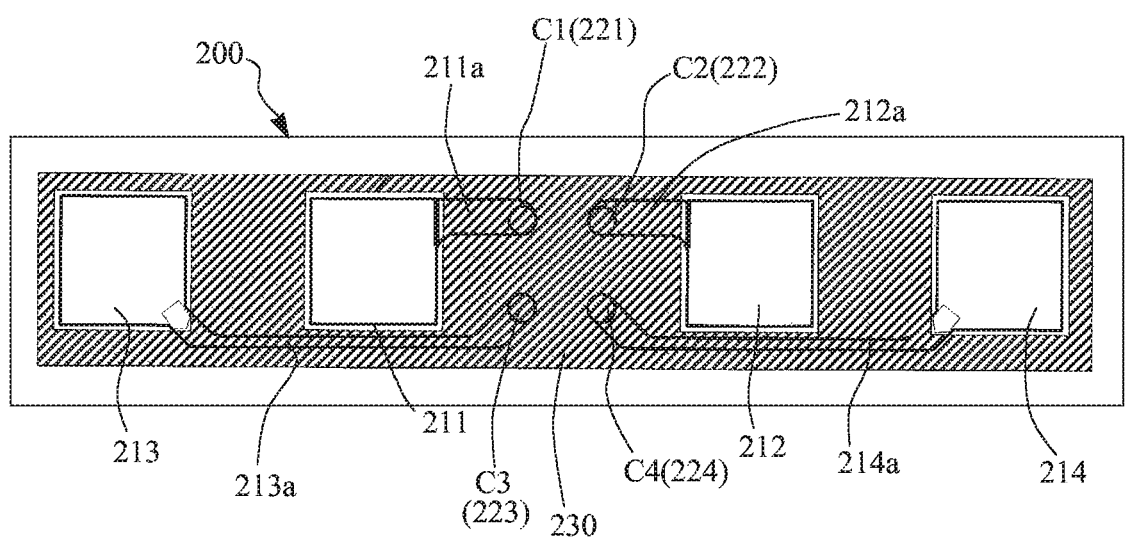
FIG. 24 is a plan view of the wearing belt having four electrodes for attaching the case to a measuring target site as viewed from a measuring target site side.

In the seventeenth embodiment, the bottom surface of the case 100 is open, as shown in FIG. 23(a). A case/wearing belt connecting substrate 131 is provided in the case 100, in addition to the substrate 10.

Although not shown in detail, the thermometer including the infrared thermometer 21, the transmitter 24, the signal processing circuit cluster 300 (described above) and the like are installed on the substrate 10.

The case/wearing belt connecting substrate 131 is disposed on the bottom surface side further than the substrate 10, and has an opening at a center portion thereof, in order to prepare a field of view of the infrared thermometer 21 and the air layer A. The case/wearing belt connecting substrate 131 of the substrate 10 is provided in the case 100 via the cylindrical support member 30 made of the heat insulating material. Furthermore, according to the seventeenth embodiment, a case thermometer 331 is provided on an inner surface of the upper lid of the case 100.

Figure 23B:
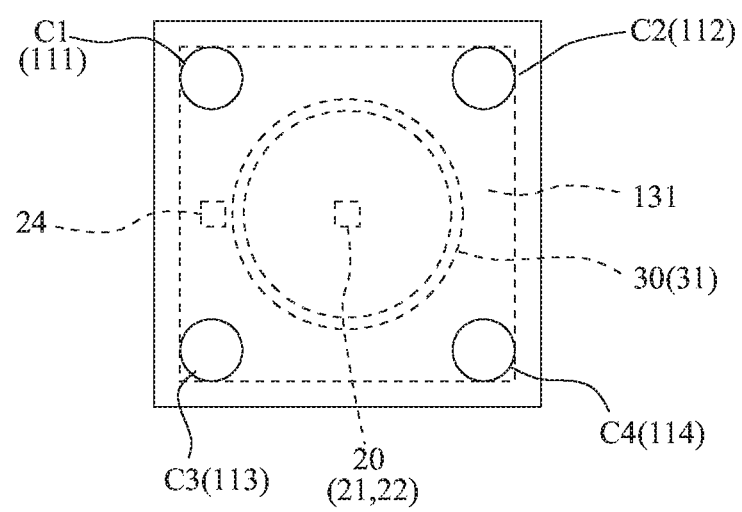
FIG. 23(b) shows a plan view of the case, as a seventeenth embodiment of the present invention.

Referring also to FIG. 23(b), the female contacts 111 to 114, respectively constituting the contact portions C1 to C4, are provided at four corners of a bottom surface of the case/wearing belt connecting substrate 131, as engaging sides of the male contacts 221 to 224 on a side of the wearing belt 200. These female contacts 111 to 114 are connected to, via the wiring, the ECG measurement circuit 310, the GSR measurement circuit 311, the GSR driving circuit 312 and the like, which are installed on the substrate 10.

In the seventeenth embodiment, the conductive magnets are adopted in the male contacts 221 to 224 and the female contacts 111 to 114, thus one-touch electrical-mechanical connection can be established.

Since the case 100 is placed on a surface side of the wearing belt 200, the infrared thermometer 21 measure a surface temperature of the wearing belt 200. Thus, in the seventeenth embodiment, the deep body temperature Tcore is calculated by adding the thermal resistance Rth of the wearing belt 200 to the thermal resistance Rth of the skin.

The surface of the wearing belt, of which temperature is measured by the infrared thermometer 21, is preferably made of a material having an infrared emissivity close to 1. As another example, the body surface temperature may be directly measured by removing the wearing belt at a portion corresponding to a solid angle of the infrared thermometer 21.

Figure 25A:
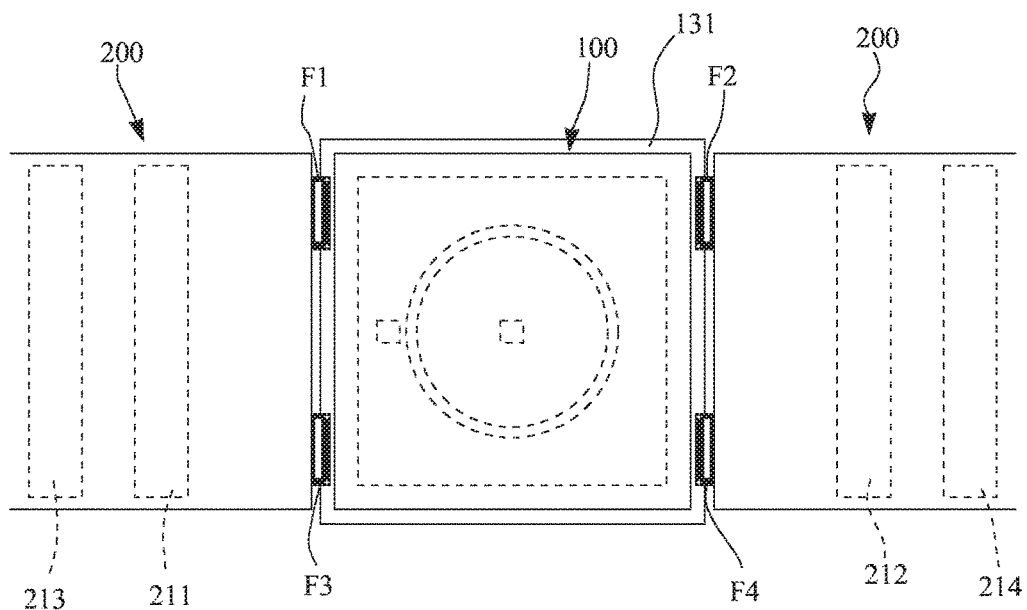
FIG. 25(a) shows a schematic plan view illustrating an aspect in which a case of a biological data measurement device is connected to a wearing belt with a detachable hook.
Figure 25B:
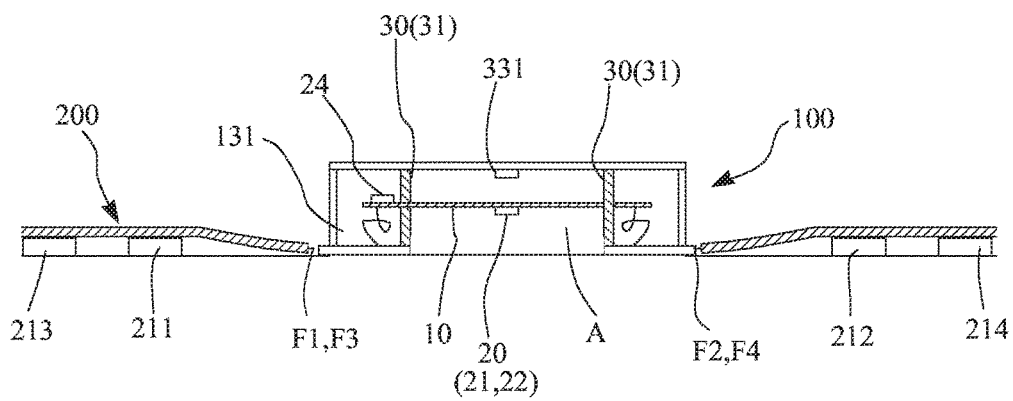
FIG. 25(b) shows a cross-sectional view thereof.
Figure 25C:
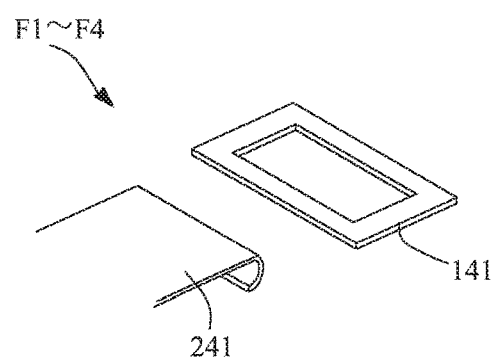
FIG. 25(c) shows an exemplified hook, as an eighteenth embodiment of the present invention.

An aspect in which the case 100 of the biological data measurement device 1 is coupled with the wearing belt 200 by a detachable hook will be described with reference to FIGS. 25(a) to 25(c), as an eighteenth embodiment of the present invention.

In the eighteenth embodiment, the case 100 is electrically and mechanically connected to the wearing belt 200 with hooks F1 to F4, instead of the contact portions C1 to C4 in the seventeenth embodiment. Each of the hooks F1 to F4 includes a combination of a female member 141 having an opening and a hook-shaped male member 241, as illustrated in FIG. 25(c).

Accordingly, in the eighteenth embodiment, the case/wearing belt connecting substrate 131 has a size to protrude from the case 100, and the female members 141 of the hooks F1 to F4 are provided at four corners thereof. On the other hand, the male members 241 of the hooks F1 to F4 are provided on the side of the wearing belt 200.

Both of the female member 141 and the male member 241 are made of a conductive material. The electrical-mechanical connection is established when the male member 241 is hooked on the female member 141. The male member 241 may be provided on a side of the case 100, and the female member 141 may be provided on the side of the wearing belt 200.

The positions of the hooks F1 to F4 correspond to the contact portions C1 to C4 in the seventeenth embodiment, respectively. Two inner electrodes 211, 212 are connected to the ECG measurement circuit 310 and the GSR measurement circuit 311 via the hooks F1, F2, while two outer electrodes 213, 214 are connected to the GSR driving circuit 312 via the hooks F3, F4.

Since the eighteenth embodiment adopts the four-electrode method, the hooks are arranged as two pairs on right and left sides. However, in a case where the two-electrode method is employed, it is enough that the hooks are arranged as one pair on right and left sides. Regardless of which configuration is adopted, the case 100 is easily attached to or detached from the wearing belt 200 according to the eighteenth embodiment. Thus, it is extremely convenient when, for example, charging a built-in battery or choosing a wearing belt.

Figure 26A:
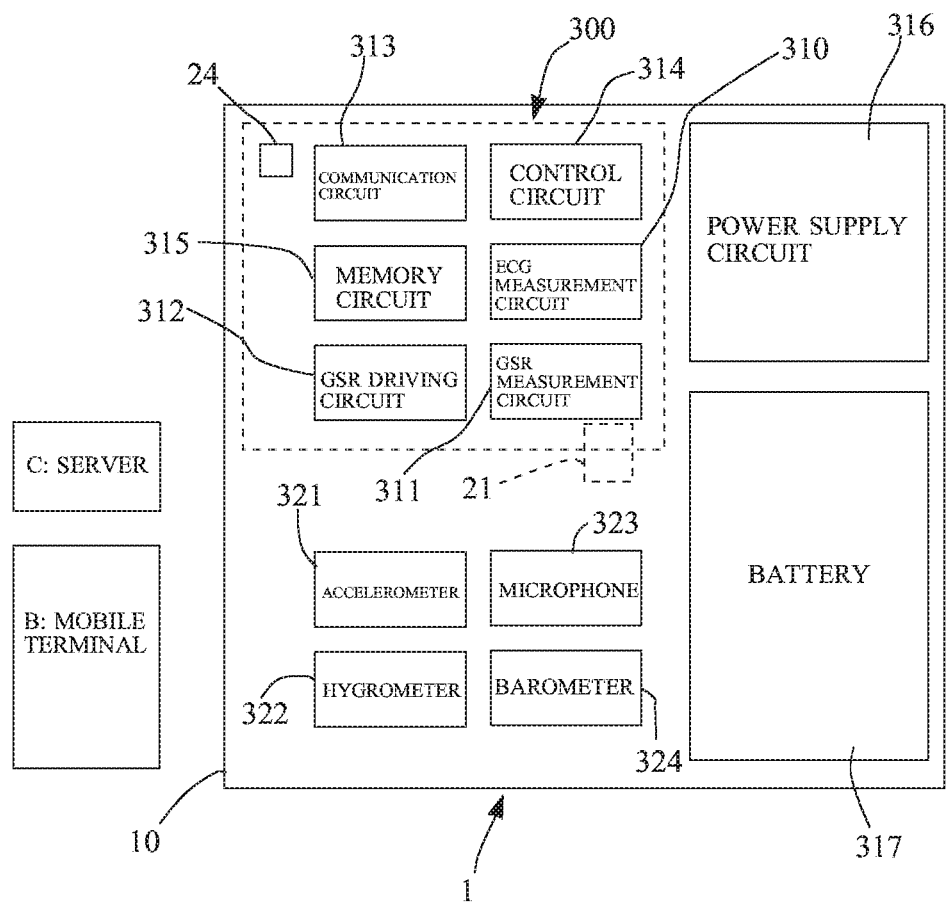
FIG. 26(a) shows a plan view illustrating an aspect in which a biological data measurement device is installed on a single substrate.
Figure 26B:
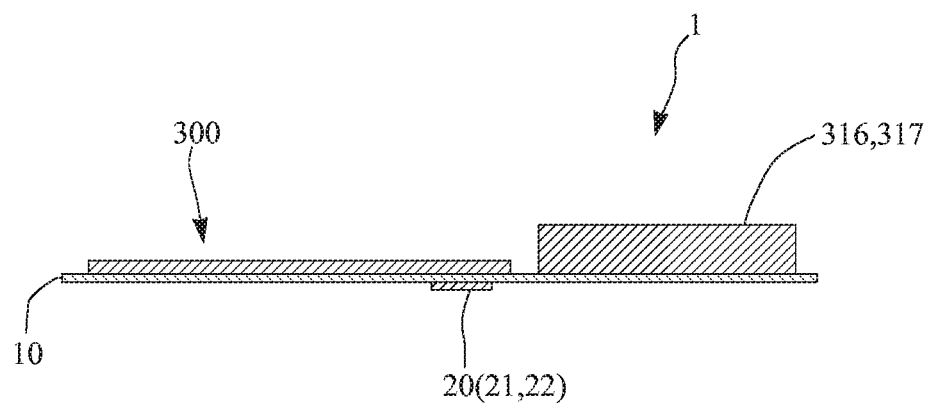
FIG. 26(b) shows a cross-sectional view thereof, as a nineteenth embodiment of the present invention.

An aspect in which the biological data measurement device 1 is installed on the single substrate 10 will be described with reference to FIG. 26, as a nineteenth embodiment of the present invention.

As described above, the biological data measurement device 1 is provided with the signal processing circuit cluster 300 including the ECG measurement circuit 310, the GSR measurement circuit 311, the GSR driving circuit 312, the communication circuit 313, the control circuit 314, and the memory circuit 315. In the nineteenth embodiment, each of these circuits is modularized and installed on the substrate 10.

SiP (system-in-package) can be used as a module. It is possible to mount an antenna (transmitter 24), a communication chip, a microcomputer (MPU) chip, a memory chip and the like within a single module.

In the nineteenth embodiment, the substrate 10 is further provided with an accelerometer 321, a hygrometer 322, a microphone 323, and a barometer 324. The infrared thermometer 21 is disposed on a rear surface side of the substrate 10 as a heat flow meter.

The microphone 323 can be used for auscultation of the chest and the abdomen. Furthermore, the microphone 323 is capable of picking up environmental sounds to determine contexts relevant to walking, vehicles, works, conference, meal, toilet, sleeping and the like. Alternatively, a voice command may be input using the microphone 323.

The biometric data collected by the biological data measurement device 1 can be sent to a mobile terminal B and processed by a CPU installed in the mobile terminal B. Furthermore, data can be sent from the mobile terminal B to a server C and processed by the server C. The processing results can be displayed on a screen of the mobile terminal B.

In accordance with the processing result, a control command may be sent to the biological data measurement device 1 in order to change the biological data acquisition conditions. The vital signs can be read by the voice instead of displaying on the screen.

For example, in a case where the user instructs to read the deep body temperature every 0.5° C. via a microphone of the mobile terminal B, the data flow is as follows.

Flow of command information: 1) speech recognition on the mobile terminal B, 2) acceptance and reply of the command on the server C, and 3) reading the replay on the mobile terminal B.

Data flow: 1) heat flow data obtained by the infrared thermometer, 2) calculation of the deep body temperature Tcore on the mobile terminal, 3) determination of 0.5° C. fluctuation, and sending read data when the condition is satisfied, on the server C, and 4) reading the data on the mobile terminal B.

Furthermore, the present invention can also be used for countermeasures against metabolic syndrome. According to the present invention, the distance body_d from the body core to the epidermis, which is unknown, is automatically obtained, thus it is possible to show to the user the decrease in the subcutaneous fat caused by the exercise.

Additionally, it is possible to show caloric expenditure due to aerobic exercise from temperature rise in the body core, heart rate, acceleration, etc., and thus the exercise effect can be enhanced.

The present invention can also be used for various biofeedback techniques (autonomous training, mindfulness, breath control, etc.). The sensors (biological data measurement device) are attached to several body regions including limbs, thereby estimating a state of vasodilatation from a peripheral core temperature, grasping a state of autonomic nerves from electrocardiographic signal fluctuation, and further measuring a breathing rate from an amplitude of the electrocardiographic signal and visualizing the breathing rate to the user. Therefore, it is possible to enhance the effects of the biofeedback techniques. Additionally, the terminal can be cooperated with the cloud in order to, for example, process, store, cite, share, and interpret by AI the data.

Figure 27A:
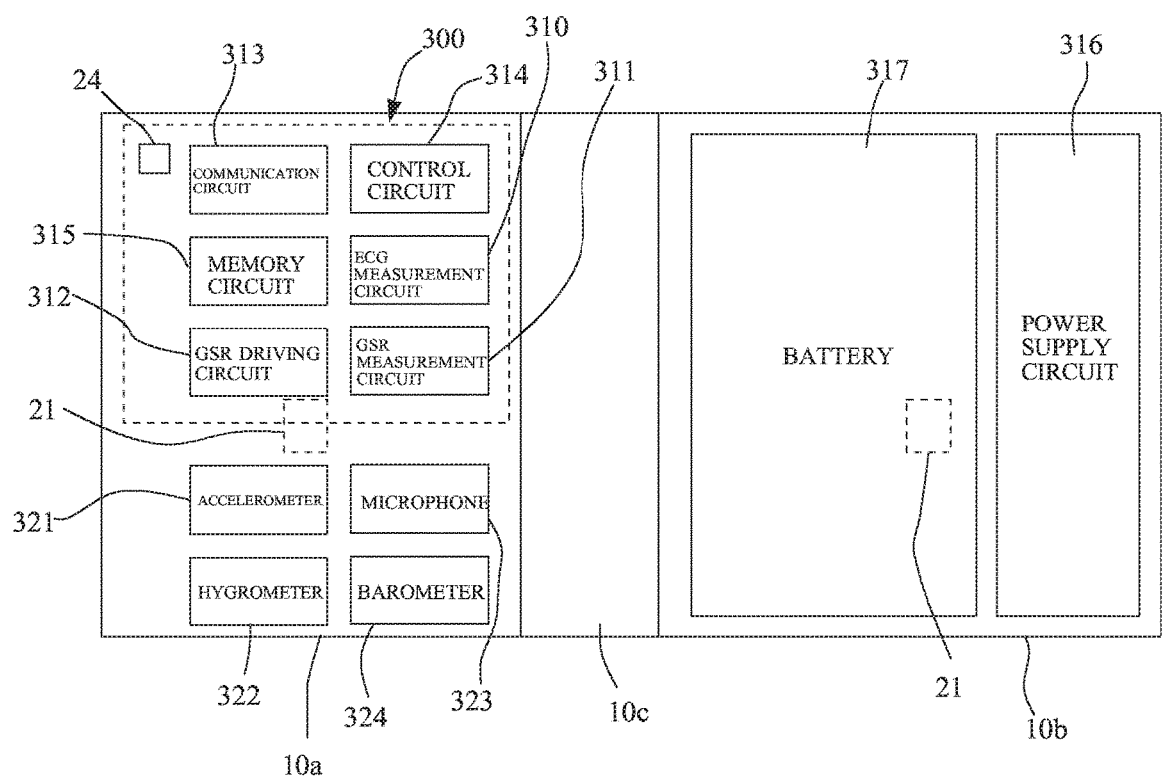
FIG. 27(a) shows a plan view illustrating an aspect in which a biological data measurement device is dividedly installed on two substrates.
Figure 27B:
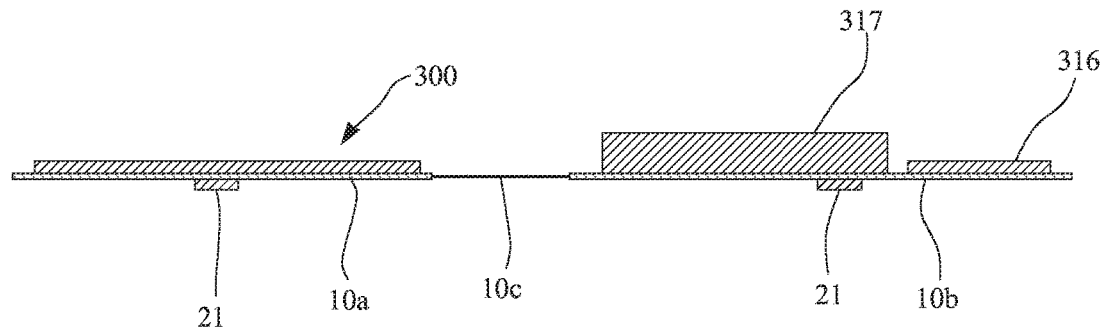
FIG. 27(b) shows a cross-sectional view thereof, as a twentieth embodiment of the present invention.

In the nineteenth embodiment, a single substrate is used as the substrate 10 on which the components are installed. However, as a twentieth embodiment of the present invention, the biological data measurement device can be dividedly installed on two substrates, i.e. a first substrate 10a and a second substrate 10b, as shown in FIG. 27.

Both of the substrates 10a, 10b are rigid substrates. In the twentieth embodiment, the modularized signal processing circuit cluster 300, the accelerometer 321, the hygrometer 322, the microphone 323 and the barometer 324 are mainly installed on one substrate, i.e. the first substrate 10a. The power supply circuit 316 and the battery 317 are installed on the other substrate, i.e. the second substrate 10b.

It is preferable that the substrates 10a, 10b have an area of about 10 mm$^2$, and are connected by a flexible substrate 10c so as to go along a curvature of the living organism. In this embodiment, the infrared thermometer 21 is installed as the heat flow meter on each of the substrates 10a, 10b. It is preferable that the flexible substrate 10c has a high thermal resistance in order to reduce the thermal interference between those heat flow meters.

Various exemplified configurations for an electrical-mechanical contact portion between the wearing belt 200 and the case 100 of the biological data measurement device 1 will be described with reference to FIGS. 28(a) to 28(e). In the following descriptions, a contact portion on the side of the case 100 is referred to as a first contact 110, and a contact portion on the side of the wearing belt 200 is referred to as a second contact 220.

Figure 28A:
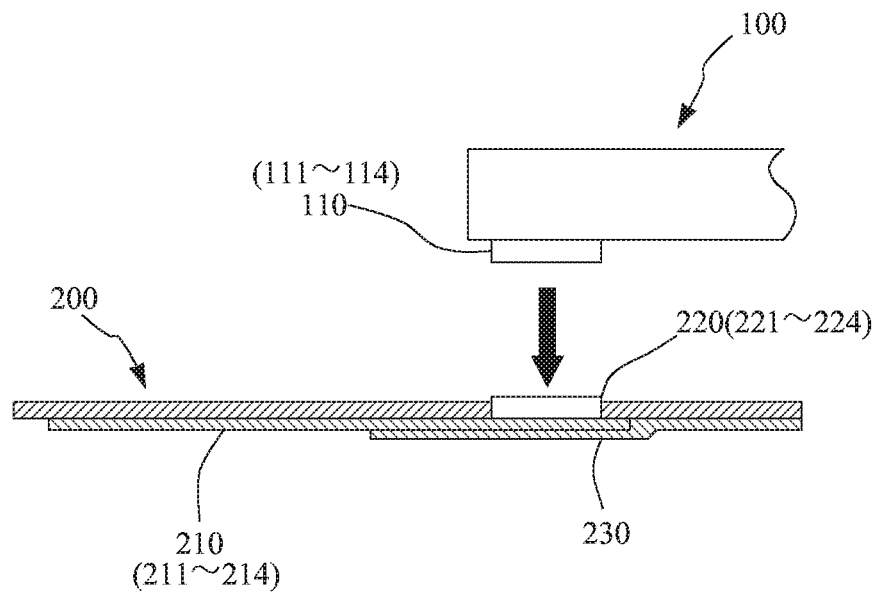
FIG. 28(a) is a schematic cross-sectional view illustrating a first example of an electrical-mechanical contact portion between a wearing belt and a case of a biological data measurement device.

First, in a first example shown in FIG. 28(a), both of the first contact 110 on the side of the case 100 and the second contact 220 on the side of the wearing belt 200 are conductive magnets. The conductive magnet is generally disk-shaped, such as a coin or a button; or alternatively, it may be a square. In a case where both the first contact 110 and the second contact 220 are the same magnets, there is an advantageous effect that center positions of the magnets are automatically aligned (matched).

The conductive magnet of the second contact 220 is electrically and mechanically connected to the electrode 210 (211 to 214) made of a conductive pattern, with a conductive adhesive, on the side of the wearing belt 200. It is possible to reduce a contact potential with the skin by using a material of which main component is silver (Ag) or silver chloride (AgCl) in the conductive pattern.

Figure 28B:
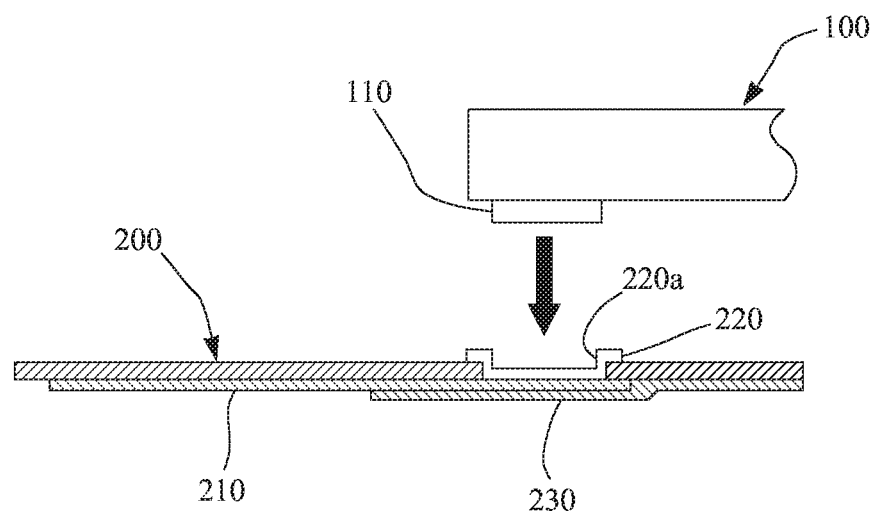
FIG. 28(b) is a schematic cross-sectional view illustrating a second example of the electrical-mechanical contact portion between the wearing belt and the case of the biological data measurement device.
Figure 28C:
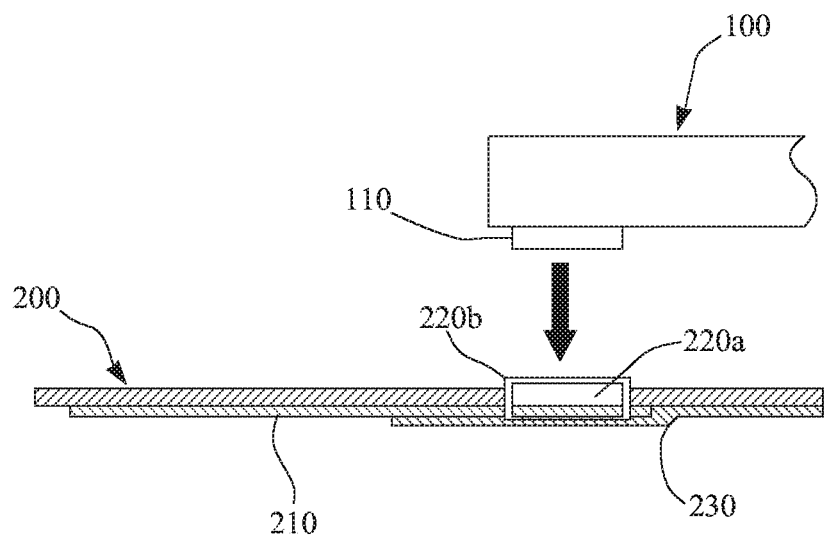
FIG. 28(c) is a schematic cross-sectional view illustrating a third example of the electrical-mechanical contact portion between the wearing belt and the case of the biological data measurement device.
Figure 28D:
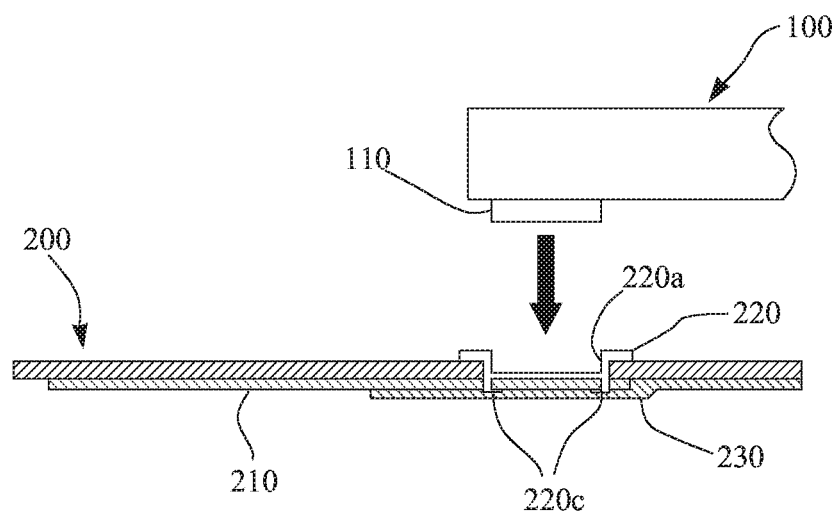
FIG. 28(d) is a schematic cross-sectional view illustrating a fourth example of the electrical-mechanical contact portion between the wearing belt and the case of the biological data measurement device.
Figure 28E:
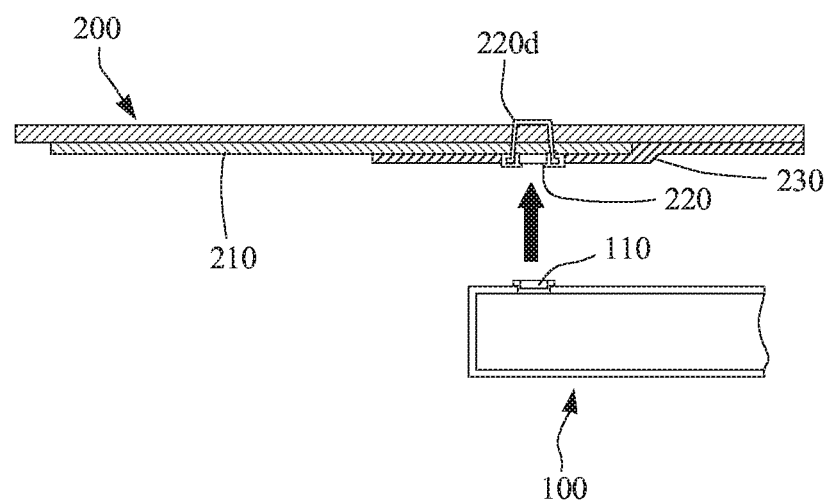
FIG. 28(e) is a schematic cross-sectional view illustrating a fifth example of the electrical-mechanical contact portion between the wearing belt and the case of the biological data measurement device.
Figure 29:
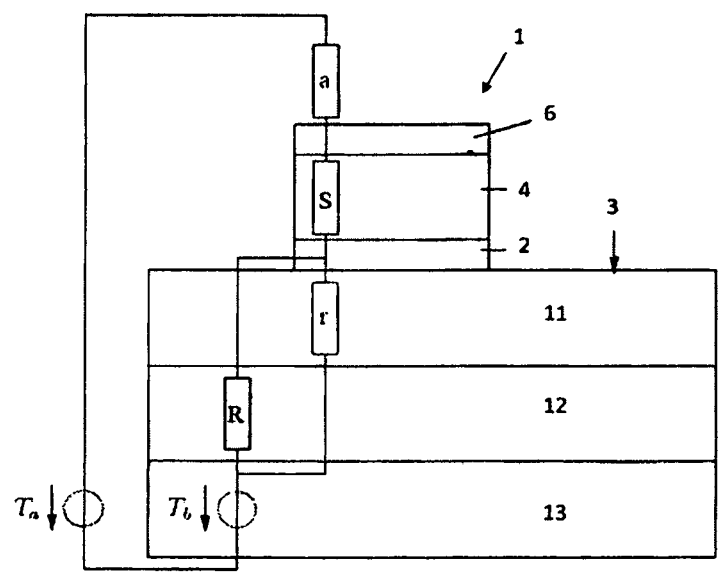
FIG. 29 is a schematic view introducing an SHF method as a first prior art.
Figure 30:
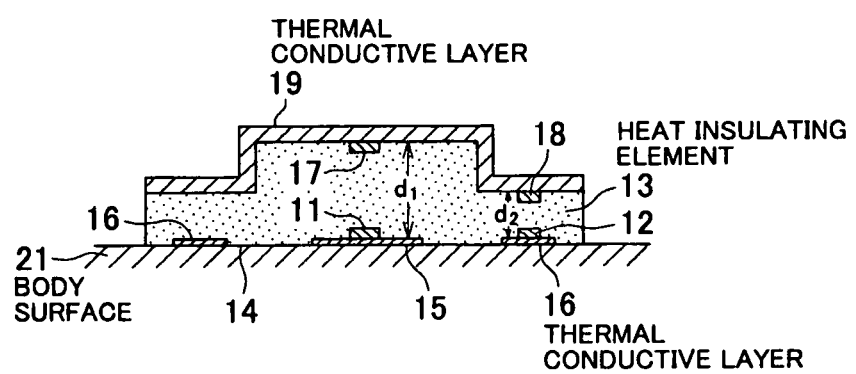
FIG. 30 is a schematic view introducing a DHF method as a second prior art.
Figure 31:
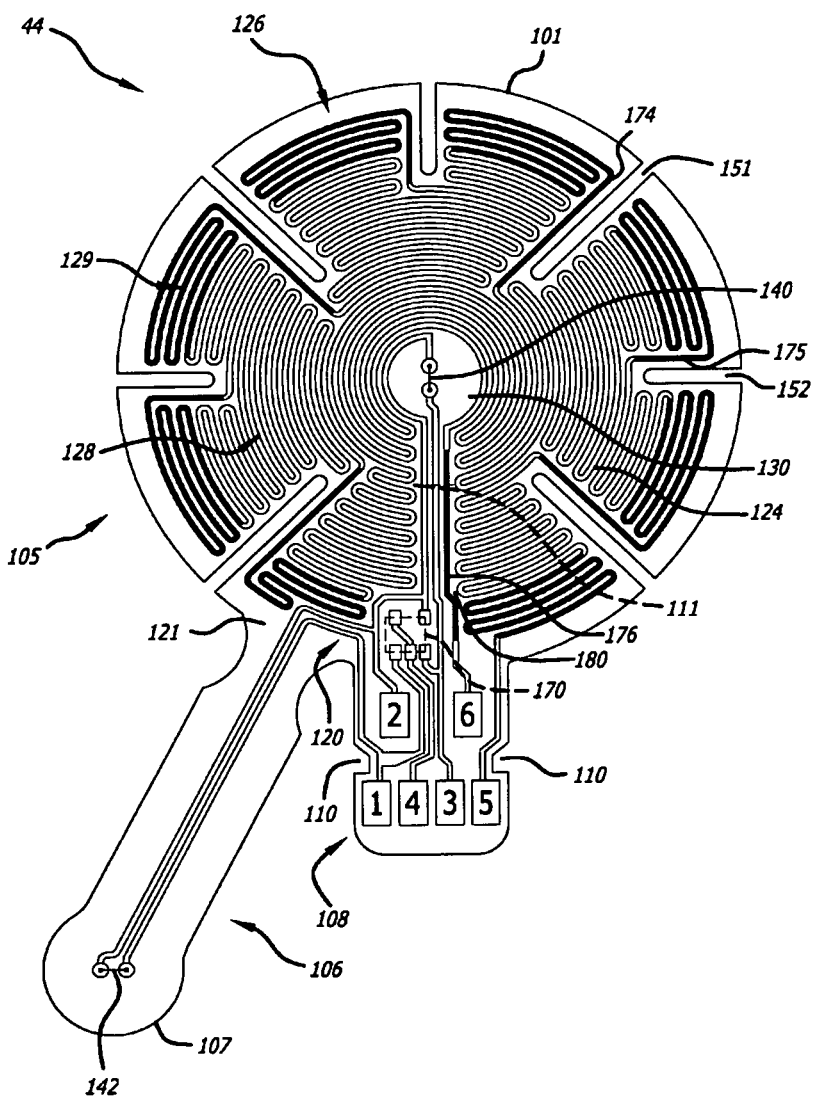
FIG. 31 is a schematic view introducing a ZHF method as a third prior art.

In a second example shown in FIG. 28(b), the first contact 110 on the side of the case 100 is a conductive magnet, while the second contact 220 on the side of the wearing belt 200 is a magnetic element having magnetism, such as iron. In this case, it is preferable to provide a recess 220a, into which the first contact 110 is fitted, on the second contact 220.

The magnetic element of the second contact 220 may be electrically and mechanically connected to the electrode 210 made of the conductive pattern, with the conductive adhesive, as in the first example. Alternatively, the magnetic element of the second contact 220 may be subjected to silver plating, and terminal fusion bonding may be performed between the silver-plated magnetic element and the silver included in the conductive pattern of the electrode 210.

A third example shown in FIG. 28(*c*) is a modified example of the first example, in which the electrode 210 is formed by the conductive pattern, and then the conductive magnet used as the second contact 220 is fixed by a gate-shaped caulking needle 220*b*. The second contact 220 is covered with an electrical insulating sheet 230 after caulking.

A fourth example shown in FIG. 28(*d*) is a modified example of the second example, in which a caulking leg 220*c* is formed on the magnetic element itself used as the second contact 220, and then the caulking leg 220*c* is embedded into the electrode 210 to fix the second contact 220. Also in this case, the second contact 220 is covered with the electrical insulating sheet 230 after caulking.

A fifth example shown in FIG. 28(*e*) is that the conductive magnetic used as the second contact 220 is disposed on the electrode 210 (below the electrode 210 in FIG. 28(*e*)) on the rear surface of the wearing belt 200, and the conductive magnetic is fixed onto the electrode 210 by punching a gate-shape caulking fitting 220*d* in the electrode 210 and the wearing belt 200 from the surface side of the wearing belt 200.

According to the fifth example, the case 100 of the biological data measurement device 1 is disposed on the rear surface side of the wearing belt 200, and pressed against and mounted onto the body surface by the wearing belt 200, as shown in FIG. 13(*a*) of the ninth embodiment.

Although the present invention has been described with reference to each of the embodiments stated above, the present invention is not limited thereto. Techniques, equivalents and the like, derived from each of the embodiments, are also encompassed in the scope of the present invention.

The invention claimed is:

1. A biological data measurement device, comprising:
a substrate disposed at a position spaced a predetermined distance from a body surface of a living organism as a measuring object via a support member so that an air layer is formed between the substrate and the body surface,
wherein the substrate is provided with a thermometer including an infrared thermometer for measuring a body surface temperature of the body surface and a substrate thermometer for measuring a substrate temperature of the substrate,
wherein the infrared thermometer is provided on a lower surface side of the substrate, opposing to the body surface, and
wherein the support member is made of a heat insulating material and forms a substantially sealed space as the air layer between the infrared thermometer and the body surface, and the heat insulating material is disposed as a cylindrical body on the lower surface side of the substrate so as to surround the air layer.

2. The biological data measurement device according to claim 1, wherein the infrared thermometer is provided with a calibration thermometer, and the calibration thermometer is used as the substrate thermometer.

3. The biological data measurement device according to claim 1, wherein a foamed plastic material is used as the heat insulating material.

4. The biological data measurement device according to claim 1, wherein the substrate is covered with the heat insulating material at a portion other than the air layer, including an upper surface thereof.

5. The biological data measurement device according to claim 1, wherein the substrate is provided with a transmitter which wirelessly transmits the body surface temperature measured by the infrared thermometer and a substrate temperature measured by the substrate thermometer.

6. The biological data measurement device according to claim 5, wherein the substrate is accommodated in a case at least partially having an electromagnetic wave transmission region in a state where the substrate is supported by a heat-insulating material.

7. The biological data measurement device according to claim 6, wherein the case is provided with a box-shaped case body of which a top surface is open and which has a bottom plate and a side plate bent upward at a substantially right angle from a peripheral edge of the bottom plate; and a lid which detachably covers the top surface of the case body.

8. The biological data measurement device according to claim 6,
wherein the case includes a box body of which a bottom surface on a body surface side is open, and which has a top plate and a side plate bent downward at a substantially right angle from a peripheral edge of the top plate,
the bottom surface is entirely covered with a sheet, and an adhesive gel is applied on a body surface side of the sheet.

9. The biological data measurement device according to claim 8, wherein the sheet and the adhesive gel are made of an infrared-transparent material.

10. The biological data measurement device according to claim 8, wherein a high thermal conductive film is provided in the case in order to transmit heat entering into and leaving from a side plate side.

11. A biological data measurement device, comprising:
a substrate disposed at a position spaced a predetermined distance from a body surface of a living organism as a measuring object via a support member so that an air layer is formed between the substrate and the body surface, and
a calculator,
wherein the substrate is provided with a thermometer including an infrared thermometer for measuring a body surface temperature of the body surface and a substrate thermometer for measuring a substrate temperature of the substrate, and
wherein, when the body surface temperature is Tsk, the substrate temperature is Tsub, a thermal resistance of the air layer is Rthair, and a heat flow that flows substantially perpendicular to the body surface is Ith, the calculator obtains the heat flow Ith from an equation (Tsk−Tsub)/Rthair.

12. The biological data measurement device according to claim 11, wherein, when a thermal resistance from a deep tissue to the body surface in the living organism is Rthbody and a deep body temperature of the living organism is Tcore, the calculator obtains the deep body temperature Tcore from an equation Tsk+Ith×Rthbody.

13. The biological data measurement device according to claim 12, further comprising in vivo electrical resistance measurement means for measuring an electrical resistance in the living organism, wherein the thermal resistance Rthbody is estimated from an in vivo electrical resistance value measured by the in vivo electrical resistance measurement means.

14. The biological data measurement device according to claim 11,
wherein a first thermometer and a second thermometer are disposed in parallel on the substrate, as the thermometer,
the first thermometer includes a first infrared thermometer for measuring the body surface temperature of the body surface and a first substrate thermometer for measuring the substrate temperature of the substrate,
the second thermometer includes a second infrared thermometer for measuring the body surface temperature of the body surface and a second substrate thermometer for measuring the substrate temperature of the substrate, and
an upper surface of the substrate, on which the first thermometer is disposed, is covered with a heat insulating material.

15. The biological data measurement device according to claim 14, further comprising a calculator for obtaining a deep body temperature Tcore of the living organism,
wherein, when the body surface temperature measured by the first thermometer is Tsk1, a heat flow that flows substantially perpendicular to the body surface is Ith1, the body surface temperature measured by the second thermometer is Tsk2, a heat flow that flows substantially perpendicular to the body surface is Ith2, and a thermal resistance from a deep tissue to the body surface in the living organism is Rthbody, the calculator calculates Rthbody from an equation (Tsk2−Tsk1)/(Ith1−Ith2) and then obtains the deep body temperature Tcore of the living organism from an equation (Ith1×Rthbody+Tsk1) or (Ith2×Rthbody+Tsk2).

* * * * *